(12) United States Patent
Kisukeda et al.

(10) Patent No.: US 11,253,540 B2
(45) Date of Patent: Feb. 22, 2022

(54) COMPOSITION INCLUDING GLYCOSAMINOGLYCAN DERIVATIVE AND CHEMOKINE RECEPTOR ACTIVITY REGULATOR

(71) Applicant: Seikagaku Corporation, Tokyo (JP)

(72) Inventors: Tomochika Kisukeda, Tokyo (JP); Yasuhiro Goto, Tokyo (JP); Yuichi Chikaraishi, Tokyo (JP); Takahiro Hatanaka, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 15/578,034

(22) PCT Filed: May 30, 2016

(86) PCT No.: PCT/JP2016/065897
§ 371 (c)(1),
(2) Date: Nov. 29, 2017

(87) PCT Pub. No.: WO2016/194869
PCT Pub. Date: Dec. 8, 2016

(65) Prior Publication Data
US 2018/0140628 A1 May 24, 2018

(30) Foreign Application Priority Data

May 29, 2015 (JP) .............................. JP2015-110784

(51) Int. Cl.
| | | |
|---|---|---|
| *A61K 31/728* | (2006.01) | |
| *A61K 31/5375* | (2006.01) | |
| *A61K 47/36* | (2006.01) | |
| *A61P 27/02* | (2006.01) | |
| *A61K 47/61* | (2017.01) | |
| *A61K 31/17* | (2006.01) | |
| *A61K 45/00* | (2006.01) | |
| *A61K 31/216* | (2006.01) | |
| *A61K 31/726* | (2006.01) | |
| *A61K 47/50* | (2017.01) | |
| *A61K 45/06* | (2006.01) | |

(52) U.S. Cl.
CPC ............ *A61K 31/728* (2013.01); *A61K 31/17* (2013.01); *A61K 31/216* (2013.01); *A61K 31/5375* (2013.01); *A61K 31/726* (2013.01); *A61K 45/00* (2013.01); *A61K 45/06* (2013.01); *A61K 47/36* (2013.01); *A61K 47/50* (2017.08); *A61P 27/02* (2018.01); *A61K 47/61* (2017.08)

(58) Field of Classification Search
CPC ........ A61P 27/00; A61P 27/02; A61K 31/726; A61K 31/727; A61K 31/728; A61K 31/737; A61K 47/36
See application file for complete search history.

(56) References Cited

U.S. PATENT DOCUMENTS

| | | | |
|---|---|---|---|
| 5,462,976 A | 10/1995 | Matsuda | |
| 5,763,504 A | 6/1998 | Matsuda | |
| 8,592,482 B2 | 11/2013 | Ambati | |
| 2007/0190055 A1* | 8/2007 | Ambati | ................ C07K 16/24 424/145.1 |
| 2007/0203089 A1 | 8/2007 | Rodrigues et al. | |
| 2008/0113935 A1* | 5/2008 | Yedgar | ................ A61K 47/544 514/56 |
| 2008/0306022 A1 | 12/2008 | Miyamoto et al. | |
| 2009/0118348 A1 | 5/2009 | Miyamoto et al. | |
| 2010/0015158 A1 | 1/2010 | Robinson et al. | |
| 2011/0207695 A1 | 8/2011 | Miyamoto et al. | |
| 2012/0087928 A1 | 4/2012 | Lashkari | |
| 2014/0120112 A1* | 5/2014 | Lashkari | ............ G01N 33/6863 424/158.1 |
| 2014/0335083 A1 | 11/2014 | Adamson et al. | |
| 2015/0196574 A1 | 7/2015 | Miyamoto et al. | |
| 2015/0320873 A1 | 11/2015 | Smejkalova et al. | |

FOREIGN PATENT DOCUMENTS

| | | |
|---|---|---|
| AU | 2012203519 | 1/2014 |
| JP | H6-73102 | 3/1994 |
| JP | 2009-511423 A | 3/2009 |
| WO | 2007/004675 A1 | 1/2007 |
| WO | 2007/079460 | 7/2007 |
| WO | 2008/005570 | 1/2008 |
| WO | 2008/059501 | 5/2008 |
| WO | 2010/129351 A1 | 11/2010 |
| WO | 2011/122321 A1 | 10/2011 |
| WO | 2013/079696 A1 | 6/2013 |
| WO | 2014/082609 A1 | 6/2014 |

OTHER PUBLICATIONS

Yu, C. et al "Redox-responsive shell-sheddable micelles self-assembled..." Chem. Eng. J., vol. 228, pp. 290-299. (Year: 2013).*
International Search Report of the International Searching Authority issued in PCT/JP2016/065897 dated Jun. 28, 2016 (2 pages).
Written Opinion of the International Searching Authority issued in PCT/JP2016/065897 dated Jun. 28, 2016 (6 pages).
Takeda, A. et al.; "CCR3 is a therapeutic and diagnostic target for neovascular age-related macular degeneration" Nature, 460(7252), Jul. 9, 2009, pp. 225-230 (16 pages).
Koo, H. et al.; "The movement of self-assembled amphiphilic polymeric nanoparticles in the vitreous and retina after intravitreal injection"; Biomaterials, vol. 33, No. 12, 2012, pp. 3485-3493 (9 pages).
Qu, Yi. et al.; "Selective non-peptide CXCR2 antagonist SB225002 inhibits choroidal neovascularization in rat model" Chinese Journal of Ophthalmology, vol. 45, No. 8, Aug. 2009, pp. 742-745 (4 pages).
The extended European search report, European Patent Office, Application. No. 16803304.1, dated Jan. 4, 2019.

(Continued)

*Primary Examiner* — Leigh C Maier
(74) *Attorney, Agent, or Firm* — Greenblum & Bernstein, P.L.C.

(57) ABSTRACT

Provided are a composition comprising a GAG derivative and a chemokine receptor activity regulator, and a pharmaceutical composition comprising said composition.

9 Claims, 11 Drawing Sheets

(56) References Cited

OTHER PUBLICATIONS

Hyoung Jo et al., "Sulodexide inhibits retinal neovascularization in a mouse model of oxygen-induced retinopathy", BMB Reports, 2014; 47(11): 637-642, www.bmbreports.org.

Japanese Office Action, Japanese Patent Office, corresponding Japanese patent application No. 2017-521934, dated Apr. 7, 2020, with English translation thereof.

* cited by examiner

COMPOSITION INCLUDING GLYCOSAMINOGLYCAN DERIVATIVE AND CHEMOKINE RECEPTOR ACTIVITY REGULATOR

TECHNICAL FIELD

The present invention relates to a composition comprising a glycosaminoglycan derivative and a chemokine receptor activity regulator, and to a pharmaceutical composition.

BACKGROUND ART

Age-related macular degeneration (hereinafter, abbreviated as "AMD"), which is a posterior eye disease involving pathological neovascularization, is broadly divided into exudative type and atrophic type. Exudative AMD is a disease with essential features of choroidal neovascularization (hereinafter, abbreviated as "CNV") and its proliferative change caused by changes in the layers of retinal pigment epithelial cells-Bruch's membrane-choroid in the macular area, which disease rapidly proceeds and causes permanent, severely reduced vision.

A kind of CC chemokine receptors (hereinafter, abbreviated as "CCR"), CCR3, is known to be expressed specifically in vascular endothelial cells in CNV collected from an exudative AMD patient (see, for example, Nature, 2009, 460: 225-230) and, in a laser-induced CNV model of mouse as an AMD pathological model, intravitreal administration of a CCR3 inhibitor suppressed CNV and has been regarded as useful for the treatment of exudative AMD (see, for example, U.S. Pat. No. 8,592,482).

Meanwhile, intravitreal administration of heparan sulfate or heparin, a sulfated glycosaminoglycan (hereinafter, glycosaminoglycan is abbreviated as "GAG"), into a laser-induced CNV model of mouse suppressed CNV and is regarded as useful for the treatment of exudative AMD (see, for example, WO 2011/122321). Further, Heebeom Koo, et al. conducted intravitreal administration of a compound of hyaluronic acid (hereinafter, abbreviated as "HA") having introduced thereinto 5β-cholanic acid and evaluated the intraocular distribution of this compound using pathological specimens (see, for example, Biomaterials, 2012, 33: 3485-3493).

CITATION LIST

Patent Literature

Patent Literature 1: U.S. Pat. No. 8,592,482
Patent Literature 2: WO 2011/122321

Non Patent Literature

Non Patent Literature 1: Nature, 2009, 460: 225-230.
Non Patent Literature 2: Biomaterials, 2012, 33: 3485-3493.

SUMMARY OF INVENTION

Problem to be Solved by Invention

However, a solution described in U.S. Pat. No. 8,592,482, which contains a specified amount or more of a solubilizing agent (such as DMSO) for preparing a CCR3 inhibitor with a concentration sufficient for exhibiting a pharmaceutical effect, may cause rapid degeneration or the like of tissues (such as lens) in the vicinity of the vitreous body. Further, Biomaterials, 2012, 33: 3485-3493 and WO 2011/122321 do not disclose or suggest any chemokine receptor activity regulator.

An object of the present invention is to provide a composition and pharmaceutical composition each exhibits, while suppressing rapid degeneration of tissues caused by administration thereof, excellent regulatory activity against chemokine receptor and excellent medicinal effects on a posterior eye disease and the like.

Means to Solve the Problem

Specific means to solve the problems described above is described below, and the present invention encompasses the following aspects.

⟨1⟩ A composition comprising a GAG derivative and a chemokine receptor activity regulator.
⟨2⟩ The composition according to item ⟨1⟩ above, wherein the GAG derivative is a hydrophobic group-introduced GAG.
⟨3⟩ The composition according to item ⟨1⟩ or ⟨2⟩ above, wherein the GAG derivative is a crosslinked GAG.
⟨4⟩ The composition according to any one of items ⟨1⟩ to ⟨3⟩ above, which comprises a covalent complex of the GAG derivative and the chemokine receptor activity regulator.
⟨5⟩ The composition according to any one of items ⟨1⟩ to ⟨4⟩ above, wherein the GAG derivative is a derivative of HA or chondroitin sulfate (hereinafter, abbreviated as "CS").
⟨6⟩ The composition according to any one of items ⟨1⟩ to ⟨5⟩ above, wherein the chemokine receptor activity regulator is a chemokine receptor antagonist.
⟨7⟩ A pharmaceutical composition comprising the composition of any one of items ⟨1⟩ to ⟨6⟩ above.
⟨8⟩ The pharmaceutical composition according to item ⟨7⟩ above, which is a drug for treating a posterior eye disease.
⟨9⟩ Use of the composition of any one of items ⟨1⟩ to ⟨6⟩ above as a drug for treating a posterior eye disease.
⟨10⟩ A method for treating a posterior eye disease, comprising administering the composition of any one of items ⟨1⟩ to ⟨6⟩ above into a vitreous body.

Effects of Invention

According to the present invention, a composition and pharmaceutical composition each exhibits, while suppressing rapid degeneration of tissues caused by administration thereof, excellent regulatory activity against chemokine receptor and excellent medicinal effects on a posterior eye disease and the like can be provided.

MODES FOR CARRYING OUT THE INVENTION

Figure 1:
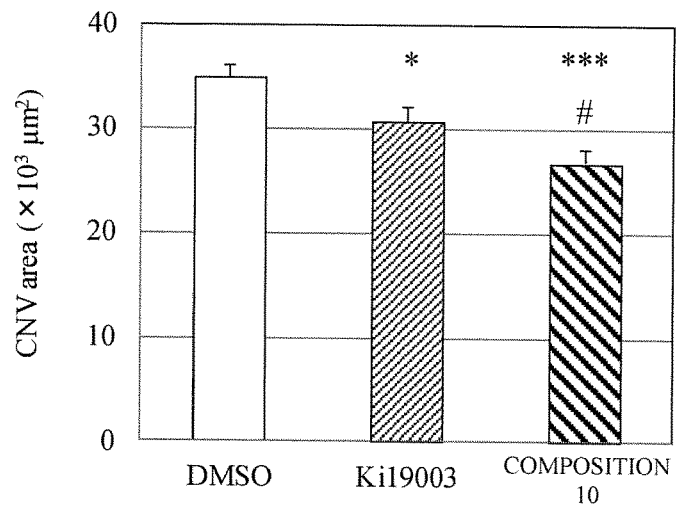
FIG. 1 is a graph illustrating CNV inhibitory effects of a Ki19003-introduced CS derivative of the present embodiment intravitreally administered to an animal model.

In the present specification, the term "step" includes not only an independent step but also a step of an aspect in which, even though the step is not distinct from another step, the intended object of the step is achieved. Further, with respect to a component in a composition, the content of the component in the composition means, when a plurality of substances each belonging to the component present in the composition, the total content of the plurality of substances, unless otherwise mentioned.

Hereinbelow, the present invention will be described in detail, referring to some embodiments of the invention.

(1) Compositions

The composition of the present invention comprises a GAG derivative and a chemokine receptor activity regulator. The composition of the present invention may contain a GAG derivative and a chemokine receptor activity regulator as compounds independent of each other, or in the form of a complex in which the GAG derivative is complexed with the chemokine receptor activity regulator by physical interaction or through a chemical bond.

Examples of the "GAG derivatives" include hydrophobic group-introduced GAGs each in which a GAG-derived group is covalently bonded to a hydrophobic group optionally via a spacer group; crosslinked GAGs each in which GAG is intramolecularly or intermolecularly crosslinked; compounds each having a GAG-derived group and a spacer group; and the like.

Examples of the "hydrophobic group-introduced GAGs" include a compound in which a hydrophobic group is covalently bonded, optionally via a spacer group, to a carboxyl group of GAG through an amide bond or ester bond or a hydroxyl group of GAG through an ether bond or ester bond. Examples of the "crosslinked GAGs" include a compound formed by covalently bonding GAGs to each other via a crosslinking group, the crosslinking group intramolecularly or intermolecularly bonding carboxyl groups or hydroxyl groups of the GAG, and a compound formed by crosslinking GAG, the crosslinking intramolecularly or intermolecularly occurring between carboxyl groups and hydroxyl groups of the GAGs via no crosslinking group.

The GAG for constituting the GAG derivative is an acidic polysaccharide having a structure composed of repetition of a disaccharide comprising an amino sugar and uronic acid (or galactose). Examples of such GAGs include HA, chondroitin, CS, dermatan sulfate and keratan sulfate. Among these, HA and CS are preferred. The acidic functional groups of the GAGs, such as a carboxyl group, may be in a free state not forming a salt or in a state forming a pharmaceutically acceptable salt.

Examples of the pharmaceutically acceptable salts include salts with alkali metal ions, such as sodium salts and potassium salts, and salts with alkaline earth metal ions, such as magnesium salts and calcium salts. Among these, from the viewpoint of compatibility and affinity to a living body, salts with pharmaceutically acceptable alkali metal ions are preferred, and sodium salts are more preferred.

The weight average molecular weight of GAG is not particularly limited and may be appropriately selected depending on the purpose or the like. As an example of the weight average molecular weight of GAG, there can be mentioned 500 Da to 10,000,000 Da, or 40,000 Da to 5,000,000 Da. The weight average molecular weight of GAG may be measured by a light scattering method.

The GAG for constituting the GAG derivative may be produced by a known method depending on the type thereof. As examples of such methods, there can be mentioned extraction and purification from animal-derived raw materials, culture and purification from GAG-producing bacteria or the like, sugar chain modification and sugar chain synthesis.

The "group derived from GAG" in the hydrophobic group-introduced GAG is a group formed by removing a hydroxyl group from a carboxyl group of GAG; a group formed by removing a hydrogen atom from a hydroxyl group or the like of GAG; or the like.

There is no particular limitation with respect to the "hydrophobic group" in the hydrophobic group-introduced GAG, and examples include a group derived from an alicyclic compound, such as cholic acid, lithocholic acid, deoxycholic acid (which are bile acids), and cholanic acid (the basic skeleton of each of the bile acids above); and a group derived from a fatty acid, such as stearic acid and oleic acid. Preferred is at least one member selected from the groups enumerated above, more preferred is a group derived from an alicyclic compound, and still more preferred is a group derived from cholanic acid, in particular, 5β-cholanic acid. The "group derived from an alicyclic compound" is a group formed by removing a hydrogen atom or hydroxyl group from the alicyclic compound, and the "group derived from a fatty acid" is a group formed by removing a hydroxyl group from a fatty acid.

There is no particular limitation with respect to the degree of substitution of the hydrophobic groups into GAG, and this ratio may be appropriately selected depending on the purpose or the like. As an example of the degree of substitution, there can be mentioned 0.1 to 80 mol %.

In the hydrophobic group-introduced GAG, the group derived from GAG may be covalently bonded to the hydrophobic group via a spacer group.

The "spacer group" is a divalent group which is capable of linking two groups though a covalent bond, and specific examples include:

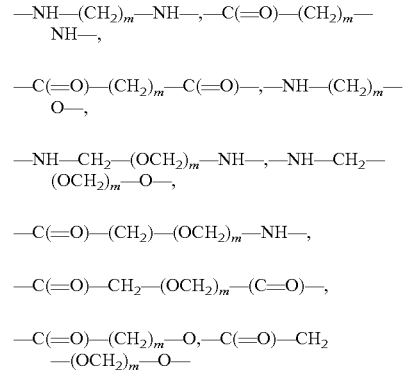

and the like. At least one member selected from these groups is preferred, and a group represented by the formula:

$$—NH—(CH_2)_m—NH— \qquad (I),$$

$$—C(=O)—(CH_2)_m—NH— \qquad (II), or$$

$$—NH—(CH_2)_m—O— \qquad (III)$$

is more preferred. In these formulae, each m independently represents an integer of 2 to 12, preferably 2 to 5, and particularly preferably 2.

The spacer group is not limited to a linear group and may have a substituent, such as an alkyl group, aryl group, hydroxyl group and halogen atom, on the methylene group contained in the spacer group. At least a part of the methylene group may be replaced with an oxygen atom, and aryl group or the like.

The hydrophobic group-introduced GAG can be produced by a usual method in which GAG, a compound to form a hydrophobic group and optionally a compound to form a spacer group are bonded together using a condensing agent or the like.

The crosslinked GAG can be formed by, for example, covalently bonding, with a crosslinking compound having two crosslinking groups, at least one of carboxyl groups and hydroxyl groups in GAG to each other via the crosslinking group. Examples of the crosslinking compounds include a compound having a photoreactive group, a polymerizable functional group, an amino group or a thiol group. A crosslinking compound having a photoreactive group or a polymerizable functional group is preferred. As examples of methods for crosslinking GAG, there can be mentioned, the methods belonging to the following four categories:

(a) crosslinking with an aldehyde crosslinking agent, such as formaldehyde or glutaraldehyde;
(b) self-crosslinking between a carboxyl group and hydroxyl group in GAG, without using a crosslinking group;
(c) crosslinking with a homo-bifunctional crosslinking agent (such as a diepoxide compound, divinyl sulfone, a diamine compound or a dihydrazide compound) or a hetero-bifunctional crosslinking agent (such as an epihalohydrin); and (d) crosslinking by reaction of GAG having introduced therein a functional group (such as a photoreactive group, a polymerizable functional group, an amino group, a thiol group or a halogen atom) with GAG having introduced therein a reactive group complementary to the above functional group or a crosslinking agent having two reactive groups as mentioned above,
although there is no particular limitation with respect to specific methods belonging to these categories.

Among these, preferred is a crosslinked GAG obtained by crosslinking of (d) above, more preferred are a crosslinked GAG obtained by photocrosslinking of GAG having introduced therein a photoreactive group and a crosslinked GAG obtained by crosslinking GAG having introduced therein a polymerizable functional group with a crosslinking agent having two thiol groups.

As an example of the photoreactive group, there can be mentioned a group derived from cinnamic acid. Such a photoreactive group may be bonded to the GAG-derived group via a spacer group, and it is preferred that a group derived from cinnamic acid is covalently bonded to GAG via a spacer group represented by formula (I), (II) or (III) above. Examples of the polymerizable functional groups include a group derived from (meth)acrylic acid. These polymerizable functional groups may be bonded to the GAG-derived group via a spacer group, and it is preferred that a group derived from (meth)acrylic acid is covalently bonded to GAG via a spacer group represented by formula (I), (II) or (III) above. Examples of the reactive groups complementary to the polymerizable functional groups include a thiol group. Examples of the crosslinking agents having two thiol groups include thiol-PEG-thiol.

There is no particular limitation with respect to the content of the crosslinking groups in the crosslinked GAG, and the content is appropriately selected depending on the purpose or the like.

The "compound comprising a GAG-derived group and a spacer group" is a compound comprising a GAG-derived group having covalently bonded thereto a spacer group at one end thereof. When the composition contains this compound, it is preferred that a group derived from the chemokine receptor activity regulator is covalently bonded to another end of the spacer group. The GAG-derived group and the spacer group are as described above, and the group derived from the chemokine receptor activity regulator is a group formed by removing a hydrogen atom or hydroxyl group from the chemokine receptor activity regulator described later.

There is no particular limitation with respect to the content of the spacer groups in the compound comprising a GAG-derived group and a spacer group, and the content is appropriately selected depending on the purpose or the like.

The "chemokine receptor activity regulator" is a compound (drug) having an effect on a chemokine receptor or a chemokine receptor-binding substance to regulate (inhibit or enhance) signal transduction via the chemokine receptor. Examples of such compounds include a chemokine receptor inhibitor, anti-chemokine antibody and chemokine receptor agonist. Examples of drugs which inhibit signal transduction via the chemokine receptor include a drug which competitively or non-competitively inhibits the chemokine receptor as a chemokine receptor antagonist. Among these, preferred are a CCR3 antagonist, CXC receptor (CXCR) 2 antagonist, CCR2 antagonist and the like. Examples of drugs which enhance signal transduction via the chemokine receptor include a drug having an effect on the chemokine receptor as a chemokine receptor agonist to increase the action of the receptor. Among these, preferred are a CXCR3 agonist and the like.

Specifically, examples of the CCR3 antagonists include Ki19003 (see, for example, WO 02/059081), SB328437 (see, for example, Journal of Biological Chemistry, 2000, 275 (47), 36626-31), GW766994 (see, for example, WO 03/082292), AZD3778 (see, for example, WO 03/004487) and the like, and examples of the CXCR2 antagonists include SB225002 (see, for example, Bioorganic & Medicinal Chemistry, 2009, 17 (23), 8102-8112). Examples of the CCR2 antagonists include RS504393 (see, for example, J. Biol. Chem., 2000, 275 (33)). Examples of the CXCR3 agonists include PS372424 (see, for example, Biochem. Biophys. Res. Commun., 2006, 349 (1), 221-8). Use of a CCR3 antagonist is particularly preferred. Some specific examples of the formulae of the chemokine receptor activity regulators are illustrated below, but the chemokine receptor activity regulators used in the present invention are not limited to those compounds.

[Chemical formula 1]

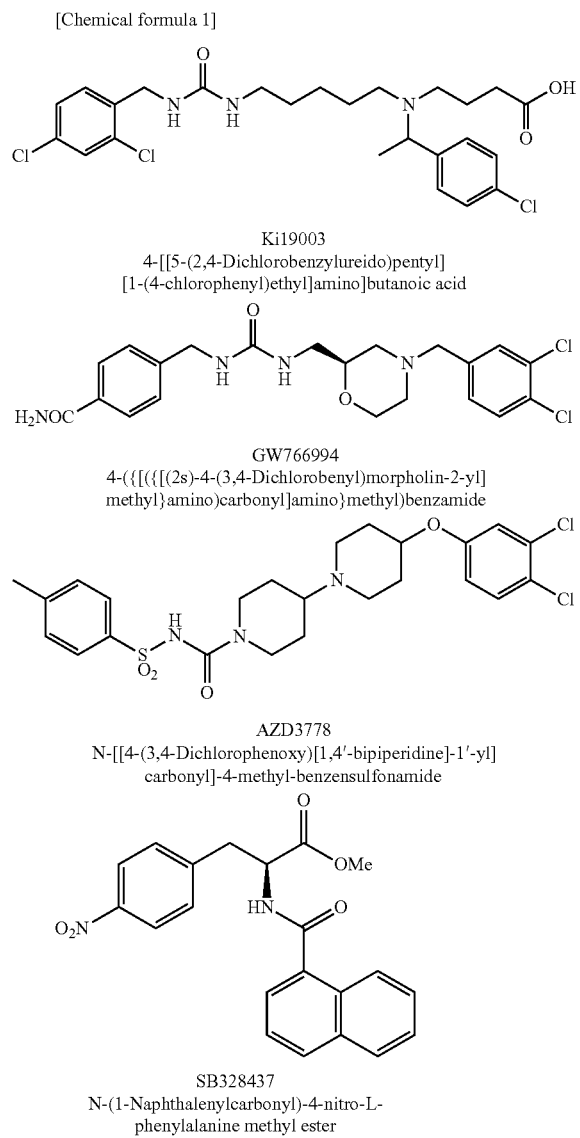

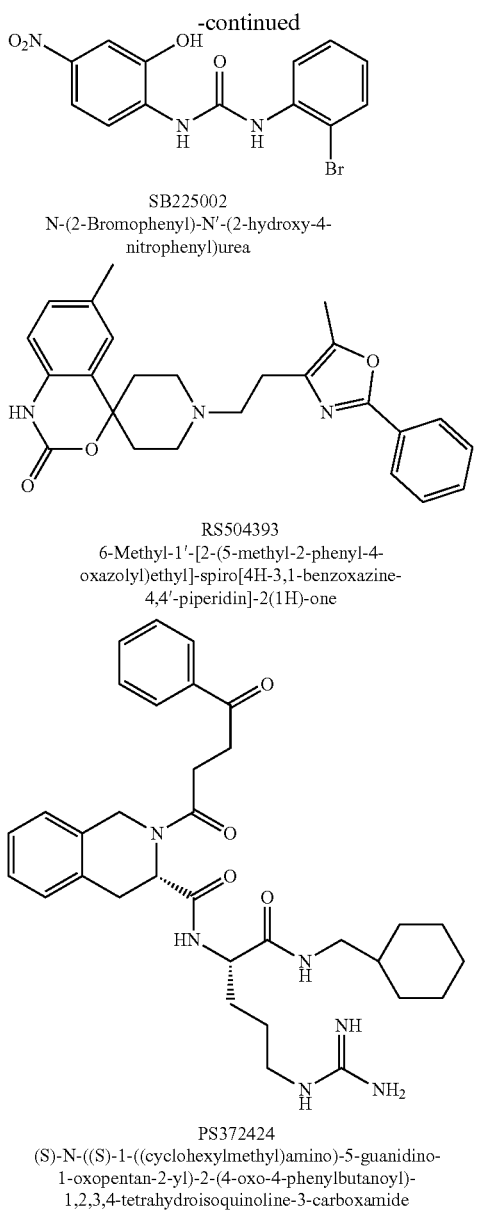

SB225002
N-(2-Bromophenyl)-N'-(2-hydroxy-4-nitrophenyl)urea

RS504393
6-Methyl-1'-[2-(5-methyl-2-phenyl-4-oxazolyl)ethyl]-spiro[4H-3,1-benzoxazine-4,4'-piperidin]-2(1H)-one PS372424
(S)-N-((S)-1-(((cyclohexylmethyl)amino)-5-guanidino-1-oxopentan-2-yl)-2-(4-oxo-4-phenylbutanoyl)-1,2,3,4-tetrahydroisoquinoline-3-carboxamide Such a chemokine receptor activity regulator may be in the form of a salt (for example, a pharmaceutically acceptable salt). Examples of the salts include a hydrochloride, hydrobromide, hydroiodide, hydrogen sulfate, hydrogenphosphate, methanesulfonate, nitrate, hydrogen maleate, acetate, hydrogen citrate, hydrogen fumarate, hydrogen tartrate, hydrogen oxalate, hydrogen succinate, benzoate and p-toluenesulfonate.

The chemokine receptor activity regulator may be contained in the composition in the form of a complex with the GAG derivative by physical interaction. A complex comprising a GAG derivative (such as a hydrophobic group-introduced GAG or crosslinked GAG) and the chemokine receptor activity regulator exhibits, while suppressing rapid degeneration of tissues caused by the administration thereof, excellent regulatory activity against chemokine receptor and excellent medicinal effects against posterior eye diseases, such as AMD.

The chemokine receptor activity regulator and the GAG derivative may be chemically bonded to each other to form a complex. Particularly preferred is a covalent complex in which a group derived from GAG is covalently bonded to a group derived from the chemokine receptor activity regulator via a spacer group. It is preferred that the covalent complex is that in which a carboxyl group in GAG and a carboxyl group in the chemokine receptor activity regulator are covalently bonded to each other via a spacer group represented by formula (III) below, and it is particularly preferred that the covalent complex is that in which a carboxyl group in GAG and a spacer group represented by formula (III) below form an amide bond:

$$—NH—(CH_2)_m—O— \quad (III)$$

wherein m is an integer of 2 to 12, preferably 2 to 5, more preferably 2.

There is no particular limitation with respect to the type of the covalent bond between the group derived from the chemokine receptor activity regulator and the spacer group in the above-mentioned covalent complex, and examples of the types of the covalent bond include an ester bond.

There is no particular limitation with respect to the method for preparing the covalent complex, the degree of substitution of the chemokine receptor activity regulator and the like, and they may be appropriately selected depending on the purpose or the like.

By the use of the composition of the present invention, intravitreal administration of a chemokine receptor activity regulator can be achieved with no use of a solubilizing agent or, even in a case in which a solubilizing agent is necessary, with an extremely small amount of a solubilizing agent, even though the regulator must be conventionally dissolved in a solubilizing agent for intravitreal administration, even when the concentration of the regulator is too low to obtain any medicinal effect by the administration of the regulator alone.

There is no particular limitation with respect to the "solubilizing agent" in the present specification, as long as the use of the agent is capable of dissolving a poorly water-soluble chemokine receptor activity regulator. Examples of the agent include organic solvents such as DMSO, polysorbate 80, macrogol 400, cyclodextrin and the like.

It is preferred that the composition of the present invention contains such a solubilizing agent (for example, an organic solvent) in an amount of 10 wt % or less, more preferably contains substantially no solubilizing agent.

Further, it is preferred that administration of the composition of the present invention into an eye causes no worsening of intraocular hemorrhage. The presence or absence of worsening of intraocular hemorrhage can be determined by the method described later in Examples.

(2) Method for Producing the Composition

Examples of embodiments of the compositions of the present invention include a mixture of the GAG derivative and chemokine receptor activity regulator and a covalent complex formed by covalently bonding the GAG derivative and chemokine receptor activity regulator. There is no particular limitation with respect to the method for mixing or covalently bonding. For example, as an example of the method for mixing, there can be mentioned a method in which a PBS solution of the GAG derivative and the chemokine receptor activity regulator dissolved in a solvent, such as ethanol, are stirred for mixing. Further, for example, as an example of the method for covalently bonding, there can be mentioned a method in which the chemokine receptor activity regulator is bonded to a functional group of the GAG derivative (preferably a GAG derivative comprising a spacer group) through an amide bond, ester bond or ether bond. Then, if necessary, the resultant composition may be further subjected to various treatments, such as dialysis, precipitation, freeze drying and concentration to dryness.

(2-1) Method for Producing the Composition Comprising the Hydrophobic Group-Introduced GAG and Chemokine Receptor Activity Regulator (2-1-1) Method for Producing the Hydrophobic Group-Introduced GAG The hydrophobic group-introduced GAG can be obtained by, for example, covalently bonding a functional group (for example, a carboxyl group) in a GAG molecule to a functional group (a carboxyl group) in a hydrophobic group via a spacer group. Although an explanation is made below, as an example of a method for producing the hydrophobic group-introduced GAG, with respect to a case in which the compound to form the hydrophobic group is 5β-cholanic acid, the method is not limited to that of this case. The hydrophobic group-introduced GAG in which the GAG-derived group and a 5β-cholanic acid-derived group are covalently bonded via a spacer can be produced, for example, by a method comprising the following steps.

The Production Method Comprising:
(A) condensing and covalently bonding (bonding through an amide bond) the carboxyl group in 5β-cholanic acid with an amino group in a spacer-forming molecule, and
(B) condensing and covalently bonding (bonding through an amide bond) the carboxyl group in GAG with an amino group in the spacer-forming molecule In step (A), the carboxyl group in 5β-cholanic acid is condensed with and covalently bonded (bonded through an amide bond) to an amino group in a spacer-forming molecule. In this case, the amino group in the spacer-forming molecule to be reacted with GAG may have been protected by a usual method, if necessary.

In step (B), a carboxyl group in GAG is condensed with and covalently bonded (bonded through an amide bond) to an amino group in the spacer-forming molecule.

There is no limitation with respect to the order of performing steps (A) and (B), as long as the method for producing the GAG derivative comprises these steps.

Examples of the spacer-forming molecules include compounds represented by the following formula:

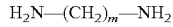

$H_2N-(CH_2)_m-NH_2$ wherein m is an integer of 1 to 12, preferably 2 to 5, and more preferably 2.

The condensation (esterification, amidation) method used for the production of the hydrophobic group-introduced GAG may be appropriately selected from usual methods. As examples of such methods, there can be mentioned a method using a condensing agent, such as a water-soluble carbodiimide (for example, 1-(3-dimethylaminopropyl)-3-ethyl-carbodiimide hydrochloride (WSC)), 4-(4,6-dimethoxy-1,3,5-triazin-2-yl)-4-methylmorpholinium chloride hydrate (DMT-MM) and dicyclohexylcarbodiimide, symmetric acid anhydride method, mixed acid anhydride methods, active ester methods and the like. The condensation reaction conditions are appropriately selected depending on the condensation reaction to be adopted.

Examples of solvents used for the condensation reaction include water, DMSO, methanol, ethanol, propanol, butanol, acetonitrile, DMF, THF, formamide, and mixtures of these solvents. Preferred are an ethanol/water mixed solvent and a DMF/formamide mixed solvent.

(2-1-2) Method for Mixing the Hydrophobic Group-Introduced GAG and Chemokine Receptor Activity Regulator The intended composition can be obtained by mixing a PBS solution of the hydrophobic group-introduced GAG and a solution of the chemokine receptor activity regulator dissolved in, for example, ethanol, and subjecting the resultant mixture to dialysis and freeze drying. There is no particular limitation with respect to the method for the mixing, dialysis and freeze drying, and the method may be appropriately selected from usual methods.

(2-2) Method 1 for Producing the Composition Comprising the Crosslinked GAG and Chemokine Receptor Activity Regulator (2-2-1) Method for Producing the Crosslinked GAG As an example of the crosslinked GAGs, a photocrosslinkable GAG can be prepared by, for example, the method described in Japanese Patent Application Kokai Publication No. 2002-249501. Specifically, the photocrosslinkable GAG can be obtained by introducing a photoreactive group (for example, a cinnamic acid derivative) to a carboxyl group in GAG by a condensation reaction. Further, the crosslinked GAG can be produced by subjecting the thus-obtained photocrosslinkable GAG to a photoreaction.

(2-2-2) Method for Mixing the Crosslinked GAG and Chemokine Receptor Activity Regulator The target composition can be prepared by stirring and mixing an aqueous solution of the above-obtained crosslinked GAG with the chemokine receptor activity regulator.

(2-3) Method 2 for Producing the Composition Comprising the Crosslinked GAG and Chemokine Receptor Activity Regulator (2-3-1) Method for Producing a Precursor of the Crosslinked GAG A precursor of the crosslinked GAG can be prepared by introducing a methacrylate group to a carboxyl group into GAG via a spacer group, if necessary, by, for example, the method described later in Examples. Examples of compounds capable of giving the crosslinked GAG by a reaction with the thus-obtained precursor of the crosslinked GAG include, but not limited to, thiol-PEG-thiol.

(2-3-2) Method for Producing the Composition

The desired composition can be obtained by, for example, mixing the precursor of the above-obtained crosslinked GAG with the chemokine receptor activity regulator and effecting a crosslinking reaction using a crosslinking agent, such as thiol-PEG-thiol.

(2-4) Method 3 for Producing the Covalent Complex of the GAG Derivative and Chemokine Receptor Activity Regulator The GAG derivative having covalently bonded thereto a chemokine receptor activity regulator can be obtained by covalently bonding a functional group in GAG (for example, a carboxyl group) and a functional group in the chemokine receptor activity regulator (for example, a carboxyl group) to each other via a spacer group.

(2-4-1) Method for Producing the GAG Having Covalently Bonded Thereto the Chemokine Receptor Activity Regulator The GAG derivative in which the GAG-derived group is covalently bonded to a group derived from the chemokine receptor activity regulator via a spacer can be produced by, for example, a method comprising the following steps.

The Production Method Comprising:

(A) condensing a carboxyl group in the chemokine receptor activity regulator with a hydroxyl group in a spacer-forming molecule to covalently bond them (bonding them though an ester bond), and (B) condensing a carboxyl group in GAG with an amino group in the spacer-forming molecule to covalently bond them (bonding them though an amide bond).

In step (A), a carboxyl group in the chemokine receptor activity regulator is condensed with and covalently bonded to a hydroxyl group in a spacer-forming molecule. The amino group in the spacer-forming molecule to be reacted with GAG may have been protected by a usual method, if necessary.

In step (B), a carboxyl group in GAG is condensed with and covalently bonded to an amino group in the spacer-forming molecule.

There is no limitation with respect to the order of performing steps (A) and (B), as long as the method for producing the GAG derivative comprises these steps.

Examples of the spacer-forming molecules include compounds each represented by the following formula:

HO—(CH$_2$)$_m$—NH$_2$ wherein m is an integer of 1 to 12, preferably 2 to 5, and more preferably 2.

The condensation (esterification and amidation) method can be appropriately selected from usual methods.

The structure of the GAG derivative may be selected from a wide variety of structures. As specific examples of the structures of the GAG derivatives, there can be mentioned, for example, with respect to CS derivatives, a structure comprising at least one occurrence of at least one structural unit represented by chemical formula (IVa) below and, with respect to HA derivatives, a structure comprising at least one occurrence of at least one structural unit represented by chemical formula (Va) below.

[Chemical formula 2]

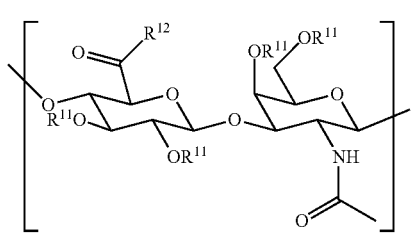
(IVa)

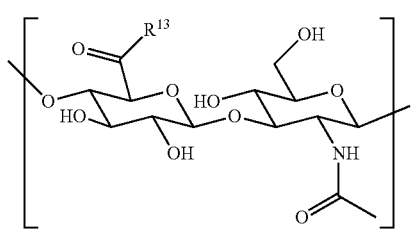
(Va)

$R^{11}$ = SO$_3$Na/H $R^{12}$, $R^{13}$ =

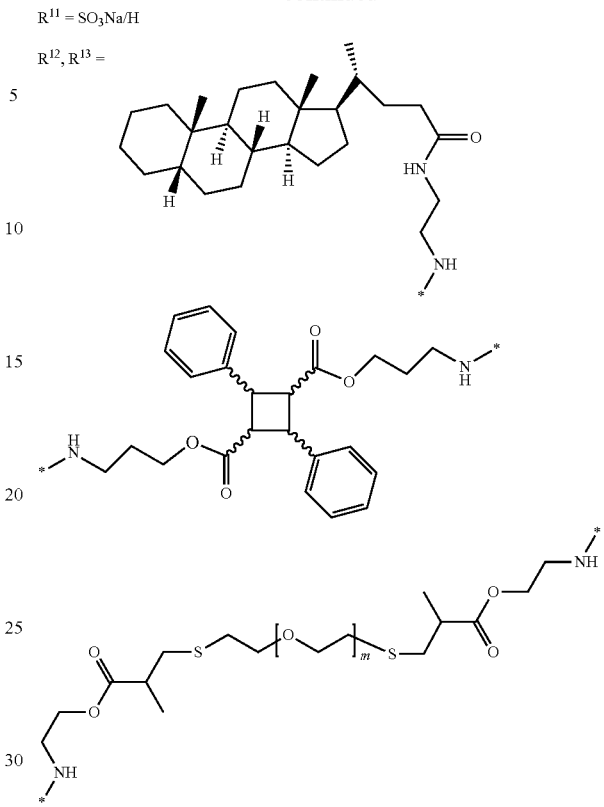

The group represented by $R^{12}$ or $R^{13}$ is covalently bonded to the GAG-derived carbonyl group at the position indicated by * in the formula.

As specific examples of the structures of the covalent complexes of the GAG derivative and chemokine receptor activity regulator, there can be mentioned, for example, when the derivative is the CS derivative, a structure comprising at least one occurrence of at least one structural unit represented by chemical formula (IVb) below and, when the derivative is the HA derivative, a structure comprising at least one occurrence of at least one structural units represented by chemical formula (Vb) below.

[Chemical formula 3]

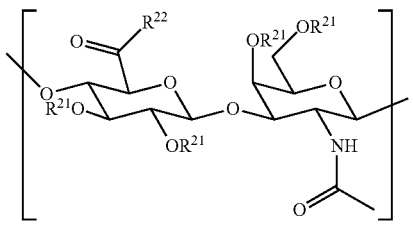
(IVb)

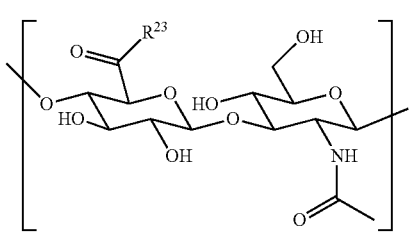
(Vb)

$R^{21}$ = SO$_3$Na/H $R^{22}, R^{23}$ =

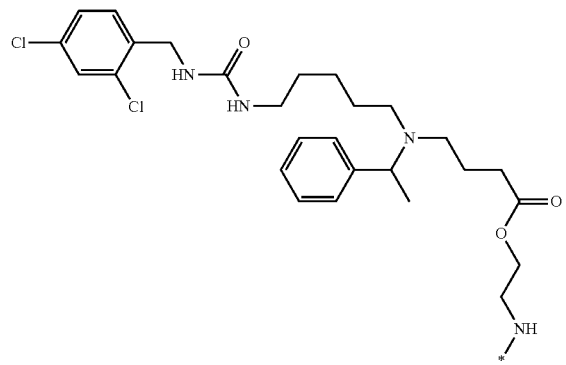

The group represented by $R^{22}$ or $R^{23}$ is covalently bonded to the GAG-derived carbonyl group at the position indicated by * in the formula.

(3) Pharmaceutical Composition

A pharmaceutical composition of the present invention comprises the composition described above, and may further contain additional components, such as a pharmaceutically acceptable excipient, if necessary. Examples of the additional components include a pharmaceutically acceptable excipient, surfactant, stabilizer and liquid medium.

There is no particular limitation with respect to the applications of the pharmaceutical composition, and it is preferred that the composition is used, for example, for the treatment of a posterior eye disease.

(4) Drug for Treating a Posterior Eye Disease

A drug for treating a posterior eye disease is a pharmaceutical composition comprising the aforementioned composition and used for the treatment of a posterior eye disease.

The term "treatment (treating)" used in the present specification means any treatment directed at a disease, such as remedy, improvement and control of a progress (prevention of worsening) of a disease.

There is no particular limitation with respect to the form of the drug for treating a posterior eye disease, as long as the drug is in the form of a pharmaceutical preparation or a medicine which can be administered to a human eye. It is preferred that the drug at the time of administration is in a liquid form, such as a solution, suspension or the like. Such a solution or suspension may be prepared for administration by dissolving a powder of the composition when needed.

The amount of the drug for treating a posterior eye disease in a liquid form for intravitreal administration is about 10 to 1000 μL.

As an example of the concentration of the drug for treating a posterior eye disease in a liquid form, there can be mentioned 0.001 to 5 wt % as the concentration of the chemokine receptor activity regulator and 0.01 to 10 wt % as the concentration of the GAG derivative.

Examples of methods for administering the drug for treating a posterior eye disease include intravitreal administration, subconjunctival administration, conjunctival sac administration, sub-Tenon administration, topical instillation, and administration to a device placed in an eye. Intravitreal administration is preferred. Among the intravitreal administrations, intravitreal injection is most preferred.

The frequency of administration of the drug for treating a posterior eye disease may be appropriately fixed depending on pathologic condition, drug concentration and the like, and the drug may be administered as required when the pathologic condition has worsened. However, the drug is not limited to be administered in these cases.

The drug for treating a posterior eye disease is to be administered to treat a posterior eye disease. The "posterior eye disease" means a disease or any other abnormality occurring at a posterior segment of an eye, which may develop into a pathological condition caused by new blood vessels or present neovascularization. Examples of such diseases and the like include diabetic retinopathy, diabetic macular edema, retinal artery occlusion, branch retinal vein occlusion (BRVO), central retinal vein occlusion (CRVO), retinopathy of prematurity, central serous chorioretinopathy, central exudative chorioretinopathy, neovascular maculopathy and AMD (exudative AMD with CNV lesion, and atrophic AMD that has a risk of CNV development and/or transitions to exudative AMD). Among these, as indications of the drug of the present invention for treating a posterior eye disease, preferred are AMD, diabetic retinopathy and diabetic macular edema, and especially preferred is exudative AMD.

As examples of embodiments of the drug for treating a posterior eye disease, there can be mentioned: a liquid preparation having a content of the solubilizing agent of not more than 10 wt %, which causes no worsening of intraocular hemorrhage; a liquid preparation comprising the crosslinked GAG and chemokine receptor activity regulator, which causes no worsening of intraocular hemorrhage; a liquid preparation comprising the crosslinked GAG and chemokine receptor activity regulator, which has the content of the solubilizing agent of not more than 10 wt % and causes no worsening of intraocular hemorrhage; a liquid preparation comprising the photocrosslinked HA and chemokine receptor antagonist, which causes no worsening of intraocular hemorrhage; a liquid preparation comprising the photocrosslinked HA and chemokine receptor antagonist, which has the content of the solubilizing agent of not more than 10 wt % and causes no worsening of intraocular hemorrhage; a liquid preparation comprising the hydrophobic group-introduced GAG and chemokine receptor activity regulator, which causes no worsening of intraocular hemorrhage; a liquid preparation comprising the hydrophobic group-introduced GAG and chemokine receptor activity regulator, which has the content of the solubilizing agent of not more than 10 wt % and causes no worsening of intraocular hemorrhage; a liquid preparation comprising the hydrophobic group-introduced CS and chemokine receptor antagonist, which causes no worsening of intraocular hemorrhage; a liquid preparation comprising the hydrophobic group-introduced CS and chemokine receptor antagonist, which has the content of the solubilizing agent of not more than 10 wt % and causes no worsening of intraocular hemorrhage; a liquid preparation comprising the CS having introduced thereinto a group derived from cholanic acid and the CCR3 inhibitor, which causes no worsening of intraocular hemorrhage; and a liquid preparation comprising the CS having introduced thereinto a group derived from cholanic acid and the CCR3 inhibitor, which has the content of the solubilizing agent of not more than 10 wt % and causes no worsening of intraocular hemorrhage. The drug of these embodiments for treating a posterior eye disease may be used as a drug for suppressing progress of exudative AMD, wherein the drug is injected into the vitreous body of a human eye.

(5) Method for Treating Posterior Eye Diseases

A method for treating a posterior eye disease comprises a step for administering into an eye the drug for treating a posterior eye disease. If necessary, the method for treating a posterior eye disease may further comprise an additional step. The method for treating a posterior eye disease may be carried out in accordance with the description in "(4) Posterior eye disease treating agents" above, and preferred conditions, administration frequency and the like of the drug are as described above.

EXAMPLES

Hereinbelow, Examples and Test Examples of the present invention will be described in greater detail, but they are not construed as limiting the technical scope of the present invention. With respect to the substituents on GAG and the chemokine receptor activity regulator, the contents in the composition were measured by the methods described later. The molecular weight of GAG is a weight average molecular weight.

(1) Preparation of GAG Derivative and Composition (Example 1) Synthesis of Aminoethyl 5β-Cholanoamide Methanol (5 ml) and concentrated hydrochloric acid (0.18 ml) were added to 5β-cholanic acid (1 g, manufactured by Aldrich), and the resultant mixture was stirred at 60° C. for 6 hours. Then, the reaction liquid was cooled to room temperature, and the precipitated solid was collected by filtration. Ethylenediamine (5 ml, manufactured by Wako Pure Chemical Industries, Ltd.) was added to the obtained compound, and the resultant mixture was stirred at 130° C. for 5 hours. After the target compound was identified by LCMS, the mixture was brought back to room temperature. The obtained solid was collected by filtration, washed with distilled water and dried to thereby obtain Compound 1 (895 mg).
ESI-MS; Calcd for $C_{267}H_{3746}N_2O$ $[M^+H]^+$, 404; found 404.

(Example 2) Synthesis of 5β-Cholanic Acid-Introduced HA

Formamide (40 ml) was added to HA (average molecular weight: about 210,000, manufactured by Lifecore Biomedical, LLC, 500 mg), and the resultant mixture was stirred at 40° C. for 2 hours while heating to give a solution. To this solution, WSC (manufactured by Wako Pure Chemical Industries, Ltd., 205 mg) and N-hydroxysuccinimide (manufactured by WATANABE CHEMICAL INDUSTRIES, LTD., 123 mg) were added, and the resultant mixture was stirred. A DMF solution (10 ml) of Compound 1 (96 mg) was added to the mixture, and further DMF (30 ml) was added. The resultant mixture was stirred at room temperature for 24 hours. The reaction liquid was put into a dialysis membrane (Spectra/Por RC Biotech Membrane MWCO 8-10 kDa, purchased from Funakoshi Co., Ltd.) and dialyzed, for 3 days in total, against methanol:distilled water=3:1, methanol:distilled water=1:1 and distilled water in this order. The dialysate was recovered and a cation-exchange resin (DOWEX™ 50 W×8, 50-100, 2 g, manufactured by Wako Chemical, Ltd.) was added. The resultant mixture was stirred for 30 minutes, and the reaction liquid was filtered and freeze dried to thereby obtain Compound 2 (590 mg). The degree of substitution of 5β-cholanic acid was 4.7 mol %.

(Example 3) Synthesis of 5β-Cholanic Acid-Introduced CS

Reactions were effected in substantially the same manner as in Example 2 using CS (average molecular weight: about 40,000, manufactured by SEIKAGAKU CORPORATION, 500 mg), to thereby obtain Compound 3 (490 mg). The degree of substitution of 5β-cholanic acid was 10.0 mol %. A drug solution for administration to animals was prepared by dissolving the freeze dried product in PBS so that the concentration was 10 mg/ml and filtering the resultant solution through a 0.22 μm filter.

(Example 4) Preparation of Ki19003-Containing HA Derivative

Ki19003 (synthesized in accordance with WO 02/059081 A2, 35 mg) was dissolved in ethanol (2 ml). To the resultant solution, Compound 2 (40 mg) synthesized in Example 2 was added in the form of a PBS (8 ml, pH 7.4) solution and dissolved therein. The resultant mixture was stirred for mixing and dialyzed (Spectra/Por RC Biotech Membrane, MWCO 3.5-5 kDa, manufactured by Spectrum Laboratories, Inc.) for 7 hours against distilled water. The dialysate was recovered, filtered through a 0.45 μm filter and freeze dried to thereby obtain Composition 4 (35 mg). The Ki19003 content was 14.0 wt %. The thus obtained Composition 4 was dissolved in PBS so that the concentration was 3 mg/ml, and the resultant solution was filtered through a 0.22 μm filter to thereby prepare a sample for administration to animals.

(Example 5) Preparation of Ki19003-Containing CS Derivative

Reactions were effected in substantially the same manner as in Example 4 using a PBS (8 ml, pH 7.4) solution of Compound 3 (35 mg) synthesized in Example 3, to thereby obtain Composition 5 (33 mg). The Ki19003 content was 22.0 wt %. The thus obtained Composition 5 was dissolved in PBS so that the concentration was 3 mg/ml, and the resultant solution was filtered through a 0.22 μm filter to thereby prepare a sample for administration to animals.

(Example 6) Preparation of GW766994-Containing HA Derivative

GW766994 (synthesized in accordance with WO 03/082292 A1, 30 mg) was dissolved in ethanol (2 ml). To the resultant solution, Compound 2 (40 mg) synthesized in Example 2 was added in the form of a PBS (8 ml, pH 7.4) solution and dispersed therein. The resultant dispersion was dialyzed (Spectra/Por RC Biotech Membrane, MWCO 3.5-5 kDa) for 7 hours against distilled water. The dialysate was recovered, filtered through a 0.45 μm filter and freeze dried to thereby obtain Composition 6 (35 mg). The GW766994 content was 23.5 wt %. The thus obtained Composition 6 was dissolved in PBS so that the concentration was 3 mg/ml, and the resultant solution was filtered through a 0.22 μm filter to thereby prepare a sample for administration to animals.

(Example 7) Preparation (1) of GW766994-Containing CS Derivative

Reactions were effected in substantially the same manner as in Example 6 using a PBS (8 ml, pH 7.4) solution of Compound 3 (35 mg) synthesized in Example 3, to thereby obtain Composition 7 (31 mg). The GW766994 content was 27.7 wt %. The thus obtained Composition 7 was dissolved in PBS so that the concentration was 3 mg/ml, and the resultant solution was filtered through a 0.22 µm filter to thereby prepare a sample for administration to animals.

(Example 8) Preparation of GW766994-Containing CS Derivative (2)

GW766994 (12 mg) was dissolved in ethanol (2 ml). To the resultant solution, Compound 3 (60 mg) synthesized in Example 3 was added in the form of a PBS (8 ml, pH 7.4) solution and stirred for mixing. The resultant mixture was dialyzed (Slide-A-Lyzer, MWCO 3.5 kDa, manufactured by Thermo Fisher Scientific Inc.) for 7 hours against distilled water. The dialysate was recovered, filtered through a 0.22 µm filter and freeze dried to thereby obtain Composition 8 (40 mg). The GW766994 content was 9.4 wt %. The thus obtained Composition 8 was dissolved in PBS so that the concentration was 10 mg/ml to thereby prepare a sample for administration to animals.

(Example 9) Synthesis of 2-Aminoethyl Esterified Ki19003

Ki19003 (190 mg) was dissolved in methylene chloride (2 ml), and dimethylaminopyridine (manufactured by Wako Pure Chemical Industries, Ltd., 13 mg), WSC (manufactured by Wako Pure Chemical Industries, Ltd., 206 mg) and N-Boc-ethanolamine (manufactured by Wako Pure Chemical Industries, Ltd., 174 mg) were added. The resultant mixture was stirred at room temperature for 3 hours under nitrogen atmosphere. After the completion of the reaction was confirmed by LCMS, the reaction liquid was washed with saturated saline, dehydrated with anhydrous magnesium sulfate, filtered and concentrated. The resultant residue was purified by silica gel chromatography (hexane:ethyl acetate=1:2) to thereby obtain a white solid (81 mg). 4 M HCl/AcOEt (10 ml, manufactured by KOKUSAN CHEMICAL Co., Ltd.) was added to this solid, and the resultant mixture was stirred at room temperature for 1 hour. After the target compound was identified by LCMS, the reaction liquid was concentrated to thereby obtain Compound 9 (71 mg).
ESI-MS; Calcd for C27H37Cl3N4O3 [M+H]$^+$, 573; found 573.

(Example 10) Synthesis of Ki19003-Introduced CS

Distilled water (4 ml) was added to CS (average molecular weight: about 40,000, manufactured by SEIKAGAKU CORPORATION, 270 mg), and the resultant mixture was stirred for 30 minutes to give a solution. To this solution, an ethanol solution (4 ml) of Compound 9 (64 mg) was added, and DMT-MM (manufactured by Wako Pure Chemical Industries, Ltd., 47 mg) was further added. The resultant mixture was stirred at room temperature overnight. Sodium chloride (270 mg) was added to the reaction liquid, and the resultant solution was added dropwise into ethanol (40 ml). The precipitated white solid was collected by filtration, washed three times with 90% ethanol in water, and dried overnight with a vacuum pump to thereby obtain Compound 10 (281 mg, degree of substitution: 18.0 wt %). The thus obtained Compound 10 was dissolved in PBS so that the concentration was 3 mg/ml, and the resultant solution was filtered again through a 0.22 µm filter to thereby obtain Composition 10, which was used as a sample for administration to animals.

(Example 11) Synthesis 2 of Ki19003-Introduced CS

A reaction was effected in substantially the same manner as in Example 10 using CS (average molecular weight: about 150,000, manufactured by SEIKAGAKU CORPORATION, 150 mg). Sodium chloride (150 mg) was added to the reaction liquid, and the resultant solution was added dropwise into ethanol (40 ml). The precipitated white solid was collected by filtration, washed three times with 90% ethanol in water, and dried overnight with a vacuum pump to thereby obtain a white solid. The thus obtained solid was dissolved in distilled water, and the resultant solution was filtered through a 0.22 µm filter and freeze dried to thereby obtain Compound 11 (91 mg, degree of substitution: 5.3 wt %). The thus obtained Compound 11 was dissolved in PBS so that the concentration was 10 mg/m to thereby obtain Composition 11, which was used as a sample for administration to animals.

(Example 12) Synthesis of 2-Aminoethyl Methacrylate Hydrochloride

To a solution of N-Boc-ethanolamine (15.5 g, manufactured by Tokyo Chemical Industry Co., Ltd.) and diisopropylethylamine (25.2 mL, manufactured by Tokyo Chemical Industry Co., Ltd.) in methylene chloride (180 mL), methacryloyl chloride (10.5 mL, manufactured by Tokyo Chemical Industry Co., Ltd.) was added dropwise under argon atmosphere at −78° C. over 3 minutes, and the resultant mixture was stirred for 1 hour, and then at room temperature for 14 hours. The reaction liquid was washed with water, extracted with methylene chloride and dried over sodium sulfate. The solid was removed by filtration, and the liquid was concentrated to thereby obtain an oil, which was then purified by silica gel chromatography (hexane:ethyl acetate=4:1). The resultant yellow solid was washed with diethyl ether and hexane to give an N-Boc ester (12.3 g) as a white solid.
$^1$H-NMR (CDCl$_3$) δ6.71 (1H, br-s), 5.75 (1H, s), 5.33-5.33 (1H, m), 4.96) 1H, br-s), 3.40-3.43 (2H, m), 3.32-3.35 (2H, m), 1.96-1.96 (3H, m), 1.44 (9H, s)
4 M HCl/Dioxane (120 mL, manufactured by KOKUSAN CHEMICAL Co., Ltd.) was added to this solid, and the resultant mixture was stirred at room temperature for 3 hours. The reaction liquid was concentrated, and the precipitated solid was washed with hexane. The solid was dried in vacuo at room temperature to afford Compound 12 (8.83 g) as a white solid.
$^1$H-NMR (D$_2$O) δ5.73 (1H, s), 5.47 (1H, s), 3.15 (2H, t, J=6.0 Hz), 2.54 (2H, t, J=6.0 Hz), 1.90 (3H, s)

(Example 13) Synthesis of Methacrylate Group-Introduced CS

CS (average molecular weight: about 40,000, manufactured by SEIKAGAKU CORPORATION, 4.03 g) was dissolved in deionized water (120 mL). To the resultant solution, Compound 12 (0.23 g) and DMT-MM (0.36 g) were sequentially added at room temperature, and the resultant mixture was stirred for 18 hours.

Sodium bicarbonate (3.0 g) was added to the reaction liquid, and the resultant mixture was stirred for 30 minutes and neutralized with acetic acid to pH 7.0. After 30 minutes of stirring, sodium chloride (12.0 g) was added, and the resultant mixture was stirred for 30 minutes. 90% Ethanol (240 mL) was added, and the resultant mixture was stirred for 30 minutes and the supernatant was discarded. 90% ethanol (240 mL) was added again, and the resultant mixture was stirred for 30 minutes and the supernatant was discarded. This operation was repeated two more times. The solid was then dialyzed (Cellulose Tube 36/32, MWCO 10 kDa, manufactured by EIDIA Co., Ltd.) against distilled water overnight and freeze dried to thereby obtain Compound 13 (4.34 g). The degree of substitution was 9.5 mol %.

(Example 14) Preparation of SB328437-Containing CS Derivative (1)

65 µL of a saline solution (0.2 mg/mL) of thiol-PEG-thiol (molecular weight: 3400, manufactured by Laysan Bio, Inc.) was added to Compound 13 (50.0 mg) and SB328437 (2.0 mg, synthesized in accordance with Journal of Biological Chemistry, 2000, 275 (47), 36626-31). Then, 135 µL of saline was added. After stirring for 1 minute, the resultant mixture was allowed to stand for 48 hours to thereby obtain a gelled compound. The gelled compound was added to saline (3 mL) and allowed to stand for 24 hours. Only the gelled compound was transferred to two sterilized syringes connected to each other at their tips, and plungers were inserted into the syringe barrels. The air inside the syringes was removed, and the two plungers were alternately pressed down 30 times. The gelled compound was then pushed out to one of the syringes to thereby obtain Composition 14, which was used as a sample for administration to animals.

(Example 15) Preparation 2 of 513328437-Containing CS Derivative (2)

Substantially the same procedure of synthesis as in Example 14 was repeated, except that the reaction was effected with the amount of the saline solution (0.2 mg/mL) of thiol-PEG-thiol of 100 µL and the amount of the subsequently added saline of 100 µL to thereby obtain Composition 15, which was used as a sample for administration to animals.

(Example 16) Preparation of SB328437-Containing CS Derivative (3)

Substantially the same procedure of synthesis as in Example 14 was repeated, except that the reaction was effected with the amount of the saline solution (0.2 mg/mL) of thiol-PEG-thiol of 200 µL to thereby obtain Composition 16, which was used as a sample for administration to animals.

(Example 17) Synthesis of Aminoethyl Oleamide

Oleic acid (500 mg, manufactured by Tokyo Chemical Industry Co., Ltd.) was dissolved in dimethylformamide (8 ml, manufactured by Wako Pure Chemical Industries, Ltd.) and, to the resultant solution, triethylamine (manufactured by Wako Pure Chemical Industries, Ltd., 0.49 ml), WSC (manufactured by Wako Pure Chemical Industries, Ltd., 408 mg), HOBT (manufactured by KOKUSAN CHEMICAL Co., Ltd., 406 mg) and N-Boc-diethylamine (manufactured by Wako Pure Chemical Industries, Ltd., 312 mg) were added. The resultant mixture was stirred at room temperature for 3 hours under nitrogen atmosphere. After the completion of the reaction was confirmed by LCMS, ethyl acetate was added to the reaction liquid, and the organic phase was sequentially washed with saturated aqueous solution of sodium bicarbonate, saturated aqueous solution of ammonium chloride and saturated saline, dehydrated over anhydrous magnesium sulfate, filtered and concentrated. The resultant residue was purified by silica gel chromatography (hexane:ethyl acetate=1:1) to thereby obtain a white solid (360 mg). Methanol (2 ml, manufactured by Wako Pure Chemical Industries, Ltd.) and 4 M HCl/AcOEt (10 ml, manufactured by KOKUSAN CHEMICAL Co., Ltd.) were added to this solid, and the resultant mixture was stirred overnight at room temperature. After the target compound was identified by LCMS, the reaction liquid was concentrated to afford Compound 17 (250 mg).

ESI-MS; Calcd for $C_{20}H_{40}N_2O$ $[M+H]^+$, 325; found 325

(Example 18) Synthesis of Oleic Acid-Introduced CS

Distilled water (20 ml) was added to CS (average molecular weight: about 40,000, manufactured by SEIKAGAKU CORPORATION, 500 mg), and the resultant mixture was stirred for 30 minutes to give a solution. An ethanol solution (20 ml) of Compound 17 (36 mg) was added, and DMT-MM (manufactured by Tokuyama Corporation, 55 mg) was further added. The resultant mixture was stirred overnight at room temperature. A 1 N aqueous solution of sodium hydroxide (2.5 mL) was added to the reaction liquid, and the resultant mixture was stirred for 30 minutes. The whole amount of the reaction liquid was put into a dialysis membrane (Slide-A-Lyzer G2, MWCO10K, 30 mL, purchased from Funakoshi Co., Ltd.), and dialyzed, for 2 days in total, against ethanol:distilled water (1:1) and distilled water in this order. The dialysate was recovered, a cation-exchange resin (DOWEX™ 50 W×8 50-100, 2 g, manufactured by Wako Chemical, Ltd.) was added and the resultant mixture was stirred for 30 minutes. The reaction liquid was filtered and freeze dried to thereby obtain Compound 18 (277 mg). The degree of substitution of 5β-oleic acid was 10.3 mol %.

(Example 19) Synthesis of GW766994-Containing Oleic Acid-Introduced CS

GW766994 (15 mg) was dissolved in ethanol (2 ml), and the resultant solution was mixed with a PBS (9 ml, pH 7.4) solution of Compound 18 (90 mg) synthesized in Example 18. The resultant solution was dialyzed (Slide-A-Lyzer G2, MWCO 3.5K, 15 mL, purchased from Funakoshi Co., Ltd.) against distilled water for 7 hours. The dialysate was recovered, filtered through a 0.22 µm filter and freeze dried to thereby obtain Composition 19 (75 mg). The GW766994 content was 8.62 wt %. The thus obtained Compound 19 was dissolved in PBS so that the concentration was 10 mg/m, and the resultant solution was filtered through a 0.22 µm filter to thereby prepare a sample for administration to animals.

(Example 20) Synthesis of Aminoethyl Lithocholamide

Lithocholic acid (500 mg, manufactured by Tokyo Chemical Industry Co., Ltd.) was dissolved in dimethylformamide (8 ml, manufactured by Wako Pure Chemical Industries, Ltd.), and WSC (manufactured by Wako Pure Chemical Industries, Ltd., 305 mg), HOBT (manufactured by KOKUSAN CHEMICAL Co., Ltd., 304 mg) and N-Boc-diethylamine (manufactured by Wako Pure Chemical Industries, Ltd., 254 mg) were added. The resultant mixture was stirred at room temperature for 3 hours under nitrogen atmosphere. After the completion of the reaction was confirmed by LCMS, ethyl acetate was added to the reaction liquid. The organic phase was washed sequentially with saturated aqueous solution of sodium bicarbonate, saturated aqueous solution of ammonium chloride and saturated saline, dehydrated over anhydrous magnesium sulfate, filtered and concentrated. The obtained residue was purified by silica gel chromatography (hexane:ethyl acetate=1:1) to thereby obtain a white solid (310 mg). THF (2 ml, manufactured by Wako Pure Chemical Industries, Ltd.) and 4 M HCl/AcOEt (10 ml, manufactured by KOKUSAN CHEMICAL Co., Ltd.) were added to this solid, and the resultant mixture was stirred at 45° C. for 1 hour. After the target compound was identified by LCMS, the reaction liquid was concentrated to afford Compound 20 (305 mg).

ESI-MS; Calcd for $C_{26}H_{46}N_2O_2$ $[M+H]^+$, 419; found 419

(Example 21) Synthesis of Lithocholic Acid-Introduced CS

Distilled water (18 ml) was added to CS (average molecular weight: about 40,000, manufactured by SEIKAGAKU CORPORATION, 400 mg), and the resultant mixture was stirred for 30 minutes to give a solution. An ethanol solution (18 ml) of Compound 20 (36 mg) was added, and DMT-MM (manufactured by Tokuyama Corporation, 55 mg) was further added. The resultant mixture was stirred overnight at room temperature. A 1 N aqueous solution of sodium hydroxide (2.0 mL) was added to the reaction liquid, and the resultant mixture was stirred for 30 minutes. The whole amount of the reaction liquid was put into a dialysis membrane (Slide-A-Lyzer G2, MWCO10K, 30 mL, purchased from Funakoshi Co., Ltd.), and dialyzed, for 2 days in total, against ethanol:distilled water (1:1) and distilled water in this order. The dialysate was recovered, a cation-exchange resin (DOWEX™ 50 W×8 50-100, 2 g, manufactured by Wako Chemical, Ltd.) was added and the resultant mixture was stirred for 30 minutes. The reaction liquid was filtered and freeze dried to thereby obtain Compound 21 (250 mg). The degree of substitution of 5β-lithocholic acid was 10.0 mol %.

(Example 22) Synthesis of GW766994-Containing Lithocholic Acid-Introduced CS

GW766994 (11 mg) was dissolved in ethanol (2 ml), and the resultant solution was mixed with a PBS (6 ml, pH 7.4) solution of Compound 21 (66 mg) synthesized in Example 21. The resultant solution was dialyzed (Slide-A-Lyzer G2, MWCO3.5K, 15 mL, purchased from Funakoshi Co., Ltd.) against distilled water for 7 hours. The dialysate was recovered, filtered through a 0.22 μm filter and freeze dried to thereby obtain Composition 22 (75 mg). The GW766994 content was 10.3 wt %. The thus obtained Composition 22 was dissolved in PBS so that the concentration was 10 mg/m, and the resultant solution was filtered through a 0.22 μm filter to thereby prepare a sample for administration to animals.

(Method for Measuring the Contents of Substituents on GAG and Chemokine Receptor Activity Regulator)
(A) Method for Measuring the Degree of Substitution of 5β-Cholanic Acid The degree of substitution of 5β-cholanic acid in each of Examples 1 and 2 was measured as follows.

$^1$H-NMR spectrum was measured in deuterated water-deuterated methanol (1:1) mixed solvent, and the ratio was calculated using the following equation:

Degree of substitution of 5β-cholanic acid(mol %)= (Integrated value for the peak assigned to the methyl group at position 21 in 5β-cholanic acid)/(Integrated value for the peaks assigned to N-acetyl groups in GAG)

(B) Method for Measuring the Degree of Substitution of Methacrylate Groups

The degree of substitution of methacrylate groups in Example 13 was measured as follows.

$^1$H-NMR spectrum was measured in deuterated water, and the ratio was calculated using the following equation:

Degree of substitution of methacrylate group(mol %)=(Integrated value for the peak assigned to methacrylate group)/(Integrated value for the peaks assigned to N-acetyl groups in GAG)

(C) Method for Measuring the Content of the Chemokine Receptor Activity Regulator
Method for Measuring the Content of Ki19003 in Examples 4 and 5

A calibration curve was prepared using a spectrophotometer (UV SPECTROPHOTOMETER manufactured by Shimadzu Corporation, measurement wavelength 220 nm), and then the measurement was carried out. The content of the drug was calculated using the following equation.

Content(wt %)=(Weight of Ki19003 in the composition)/(Weight of the composition)×100

Method for Measuring the Content of GW766994 in Examples 6, 7 and 8

A calibration curve was prepared by HPLC under the following conditions, and then the measurement was carried out.
Column: ODS-3, 4.6×150 mm, 5 um (manufactured by GL Science)
Flow: 0.8 ml/min
Detect: 225 nm
Eluent: acetonitrile: 20 mM aqueous solution of ammonium acetate=5:5 (isocratic)

The content of the drug was calculated using the following equation.

Content(wt %)=(Weight of GW766994 in the composition)/(Weight of the composition)×100

Method for Calculating the Content of Ki19003 in Examples 10 and 11

Compound 10 or 11 (with a known measured weight) was hydrolyzed by heating at 37° C. for 2 hours in a 2 M aqueous solution of sodium hydroxide. A calibration curve for Ki19003 was prepared by HPLC under the following conditions, and then the measurement of the liberated Ki19003 was carried out.
Column: ODS-3, 4.6×150 mm, 5 um (manufactured by GL Science)
Flow: 0.8 ml/min
Detect: 225 nm
Eluent: acetonitrile: 50 mM aqueous solution of formic acid=3:7 (isocratic)

The content was calculated using the following equation.

Content(wt %)=(Weight of Ki19003 liberated from the compound)/(Weight of the compound)×100

(2) Evaluation Methods (Test Example 1) Assay of CNV Inhibitory Effects Using Composition 10

Laser-induced CNV models of rat were prepared, and neovascularization inhibitory effect was examined with respect to intravitreal administration of Composition 10 or Ki19003.

⟨Test Substances⟩

Ki19003 was dissolved in DMSO to obtain a solution of Ki19003 (0.6 mg/mL).

The following test substances were used in the assay.
1) Composition 10 (containing 0.54 mg/mL of Ki19003)
2) Ki19003 (0.6 mg/mL)
3) DMSO (The sample for administration to animals prepared in Example 10 was used as Composition 10.)

⟨Method⟩

(1) Preparation of Laser-Induced CNV Models and Administration of the Test Substance BN/CrlCrlj rats (male, CHARLES RIVER LABORATORIES JAPAN, INC.) were used for the preparation of animal models. Under general anesthesia by intraperitoneal administration of an anesthetic mixture (saline:Somnopentyl=9:1) (about 2 mL/body), Mydrin-P ophthalmic solution was topically instilled to cause mydriasis in both eyes. The retina around the optic disk was irradiated with a laser beam to induce CNV. Used for the laser beam irradiation were SCOPISOL solution for eye, Fundus 5.4 mm Laser Lens, a laser photocoagulation device and a slit lamp illumination system. Immediately after the laser beam irradiation, 5 μL/eye of the test substance was administered once into the vitreous bodies of both eyes. Immediately after the administration, one drop of an antimicrobial drug (VEGAMOX Ophthalmic Solution 0.5%) was instilled.

(2) Preparation of Flat Mounts

After 10 days from the preparation, the models were euthanized with $CO_2$. The eyeballs were extracted and immersed in 10% neutral buffered solution of formalin (room temperature, about 60 minutes). Eye cups were prepared, washed with PBS, dehydrated with methanol and immersed in PBS containing 1% bovine serum albumin and 0.5% Triton X-100 (room temperature, about 60 minutes). The retina was removed, and 60 μL of 0.5% fluorescein *Griffonia simplicifolia* lectin I, FITC-conjugate was added to the eye cups, and the eye cups were allowed to stand (under refrigeration, overnight). By this treatment, vascular endothelial cells of CNV were fluorescently stained with FITC-lectin. Eight slits were made radially in each of the eye cups to thereby obtain flat mounts. These flat mounts were washed twice with PBS containing 0.1% Triton X-100 and embedded on a glass slide with about 120 μL of Prolong Gold Antifade Reagent.

(3) Imaging and Area Measurement of CNV

A fluorescence image of CNV in the flat mount embedded on a glass slide was taken with a fluorescent microscope. The area of CNV was measured using an image processing software (Image pro exp).

⟨Statistical Analysis⟩

The areas of CNV in each group were analyzed by a test (t-test) for unpaired two groups. The significance level was 5% on both sides.

⟨Results of Assay⟩

The results of measurement of the CNV area are given in the table below and FIG. 1.

Composition 10 showed significant inhibitory effects of CNV, as compared to DMSO and Ki19003.

TABLE 1

|  | mean | S.E. | n | Test results |
|---|---|---|---|---|
| DMSO | 34980 | 1125 | 16 |  |
| Ki19003 | 30752 | 1371 | 14 | * |
| Composition 10 | 26811 | 1206 | 16 | ***, # |

\* $P < 0.05$,
\*\*\* $P < 0.001$ (vs. DMSO), t-test
\#: $P < 0.05$ (vs. Ki19003), t-test (Test Example 2) Assay of CNV Inhibitory Effects Using Composition 11 (1)

Laser-induced CNV models of rat were prepared, and neovascularization inhibitory effect was examined with respect to intravitreal administration of Composition 11 or Ki19003.

⟨Test Substances⟩

Ki19003 was dissolved in DMSO to obtain a solution of Ki19003 (0.53 mg/mL). The following test substances were used in the assay.
1) Composition 11 (containing 0.53 mg/mL of Ki19003)
2) Ki19003 (0.53 mg/mL)
3) DMSO (The sample for administration to animals prepared in Example 11 was used as Composition 11.)

⟨Method⟩

Substantially the same procedure as in ⟨Method⟩ for Test Example 1 was repeated.

⟨Statistical Analysis⟩

The areas of CNV in each group were analyzed by a test (t-test) for unpaired two groups. The significance level was 5% on both sides.

⟨Results of Assay⟩

Figure 2:
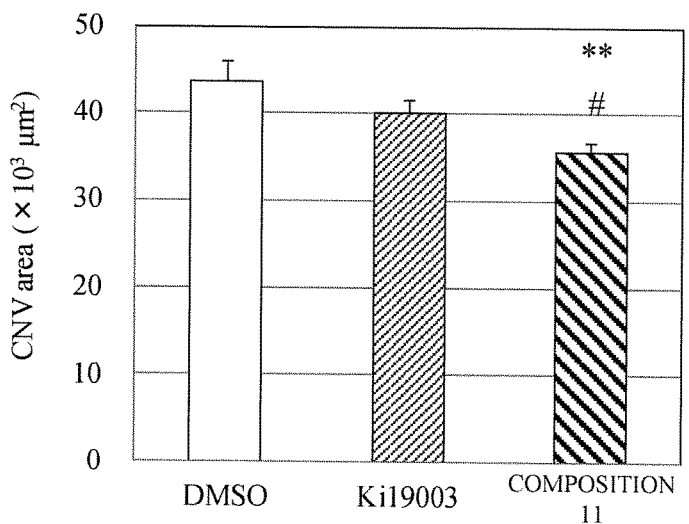
FIG. 2 is a graph illustrating CNV inhibitory effects of a Ki19003-introduced CS derivative of the present embodiment intravitreally administered to an animal model.

The results of measurement of the CNV area are given in the table below and FIG. 2.

Composition 11 showed significant inhibitory effects of CNV, as compared to DMSO and Ki19003.

TABLE 2

|  | mean | S.E. | n | Test results |
|---|---|---|---|---|
| DMSO | 43613 | 2344 | 9 |  |
| Ki19003 | 40222 | 1419 | 10 | N.S. |
| Composition 11 | 35660 | 1064 | 10 | **, # |

\*\* $P < 0.01$ (vs. DMSO), t-test
\#: $P < 0.05$ (vs. Ki19003), t-test
N.S.: Not Significant (vs. DMSO), t-test ⟨Conclusions⟩

It was shown from Test Examples 1 and 2 that Ki19003-introduced CS can be used as a drug for treating a posterior eye disease, especially AMD, which exhibited medicinal effects higher than those of Ki19003. It was also shown that CS could be used as GAG to constitute a GAG derivative.

(Test Example 3) Assay of CNV Inhibitory Effects Using Composition 11 (2)

Laser-induced CNV models of rat were prepared, and neovascularization inhibitory effect was examined with respect to intravitreal administration of Composition 11 or a formulation comprising CS and Ki19003.

Figure 3:
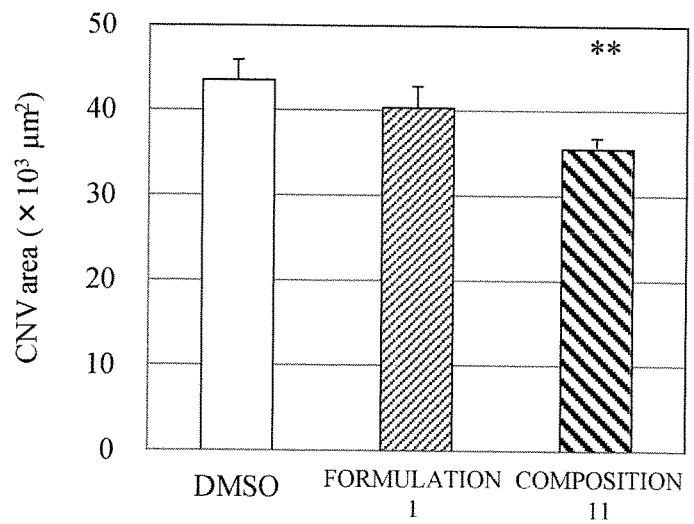
FIG. 3 is a graph illustrating CNV inhibitory effects of a Ki19003-introduced CS derivative of the present embodiment intravitreally administered to an animal model.

⟨Test Substances⟩
CS (19 mg, the same as that used in Example 11, manufactured by SEIKAGAKU CORPORATION) and Ki19003 (1 mg) were mixed together with PBS (2 mL). The resultant mixture was shaken to give a formulation comprising CS and Ki19003 (hereinbelow "Formulation 1"). The following test substances were used in the assay.
1) Composition 11 (containing 0.53 mg/mL of Ki19003)
2) Formulation 1 (containing 0.5 mg/mL of Ki19003)
3) DMSO
(The sample for administration to animals prepared in Example 11 was used as Composition 11.)
⟨Method⟩
Substantially the same procedure as in ⟨Method⟩ for Test Example 1 was repeated.
⟨Statistical Analysis⟩
The areas of CNV in each group were analyzed by a test (t-test) for unpaired two groups. The significance level was 5% on both sides.
⟨Results of Assay⟩
The results of measurement of the CNV area are given in the table below and FIG. 3.
Composition 11 showed significant inhibitory effects of CNV, as compared to DMSO.

TABLE 3

|  | mean | S.E. | n | Test results |
|---|---|---|---|---|
| DMSO | 43613 | 2344 | 9 |  |
| Formulation 1 | 40385 | 2438 | 10 | N.S. |
| Composition 11 | 35660 | 1064 | 10 | ** |

** P < 0.01 (vs. DMSO), t-test
N.S.: Not Significant (vs. DMSO), t-test

⟨Conclusions⟩
Ki19003-introduced CS was shown to be able to be used as a drug for treating a posterior eye disease, especially AMD, which exhibited medicinal effects higher than those of a formulation comprising CS and Ki19003. It was also shown that a mere blend of GAG and a chemokine receptor antagonist is not satisfactory as a drug for treating a posterior eye disease, and the usefulness of a covalent complex of the GAG derivative with the chemokine receptor antagonist was thus confirmed.

(Test Example 4) Assay of CNV Inhibitory Effects Using Compositions 14, 15 and 16

Figure 4:
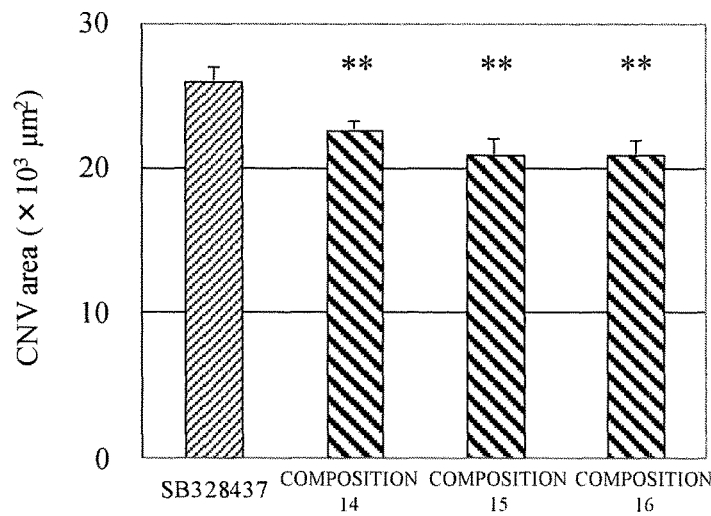
FIG. 4 is a graph illustrating CNV inhibitory effects of the composition of the present embodiment comprising SB328437 and a CS derivative, the composition intravitreally administered to an animal model.

Laser-induced CNV models of rat were prepared, and neovascularization inhibitory effect was examined with respect to intravitreal administration of each of Compositions 14, Composition 15, Composition 16 and SB328437.
⟨Test Substances⟩
SB328437 was dissolved in DMSO to obtain a solution of SB328437 (2 mg/mL). The following test substances were used in the assay.
1) Composition 14 (containing 1.33 mg/mL of SB328437)
2) Composition 15 (containing 1.67 mg/mL of SB328437)
3) Composition 16 (containing 3.33 mg/mL of SB328437)
4) SB328437 (2 mg/mL)
(The samples for administration to animals prepared in Examples 14, 15 and 16 were used as Compositions 14, 15 and 16, respectively.)
⟨Method⟩
Substantially the same procedure as in ⟨Method⟩ for Test Example 1 was repeated.
⟨Statistical Analysis⟩
The areas of CNV in each group were analyzed by a test (t-test) for unpaired two groups. The significance level was 5% on both sides.
⟨Results of Assay⟩
The results of measurement of the CNV area are given in the table below and FIG. 4.
Each of Compositions 14, 15 and 16 showed significant inhibitory effects of CNV, as compared to SB328437.

TABLE 4

|  | mean | S.E. | n | Test results |
|---|---|---|---|---|
| SB328437 | 26040 | 933 | 8 |  |
| Composition 14 | 22647 | 628 | 8 | ** |
| Composition 15 | 20957 | 1079 | 8 | ** |
| Composition 16 | 20953 | 1015 | 8 | ** |

** P < 0.01 (vs. SB328437), t-test

⟨Conclusions⟩
The composition comprising SB328437 and the crosslinked CS was shown to be able to be used as a drug for treating posterior eye disease, especially AMD, which exhibited medicinal effects higher than those of SB328437. The crosslinked GAG was shown to be able to be used as the GAG derivative, and CS was shown to be able to be used as GAG. Further, SB328437 was shown to be able to be used as a chemokine receptor antagonist.

(Test Example 5) Assay of CNV Inhibitory Effects Using a Composition Comprising SB225002 and Crosslinked HA (Gel-One)

Figure 5:
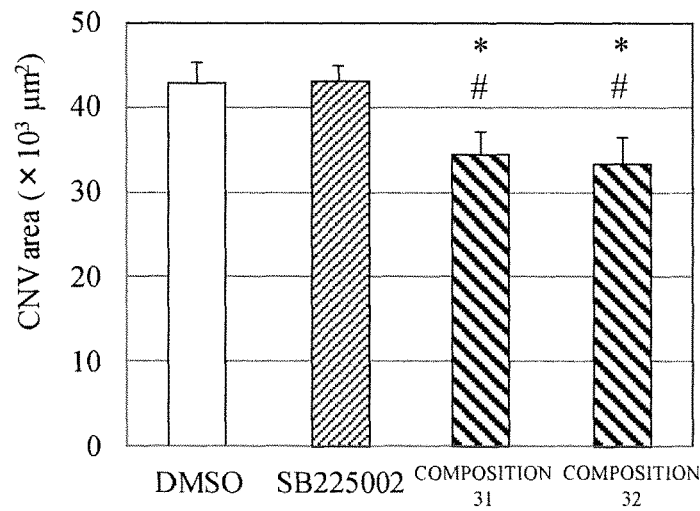
FIG. 5 is a graph illustrating CNV inhibitory effects of the composition of the present embodiment comprising SB225002 and an HA derivative, the composition intravitreally administered to an animal model.

Laser-induced CNV models of rat were prepared, and neovascularization inhibitory effect was examined with respect to intravitreal administration of each of a composition comprising SB225002 and Gel-One (photocrosslinked HA: manufactured by SEIKAGAKU CORPORATION) as well as SB225002.
⟨Test Substances⟩
SB225002 (synthesized in accordance with Bioorganic & Medicinal Chemistry, 2009, 17 (23), 8102-8112) was dissolved in DMSO to obtain a solution of SB225002 (0.02 mg/mL). SB225002 was dissolved in DMSO to obtain a solution of SB225002 (0.2 mg/mL), and 0.15 mL of the resultant SB225002 (0.2 mg/mL) solution was mixed with Gel-One (1.5 mL) and stirred to thereby obtain Composition 31. SB225002 was dissolved in DMSO to obtain a solution of SB225002 (2 mg/mL), and the resultant 2 mg/mL solution of SB225002 (0.015 mL) was mixed with Gel-One (1.5 mL) and stirred to thereby obtain Composition 32. The following test substances were used in the assay.
1) Composition 31 (containing 0.018 mg/mL of SB225002)
2) Composition 32 (containing 0.02 mg/mL of SB225002)
3) SB225002 (0.02 mg/ml)
4) DMSO
⟨Method⟩
Substantially the same procedure as in ⟨Method⟩ for Test Example 1 was repeated.
⟨Statistical Analysis⟩
The areas of CNV in each group were analyzed by a test (t-test) for unpaired two groups. The significance level was 5% on both sides.
⟨Results of Assay⟩
The results of measurement of the CNV area are given in the table below and FIG. 5.

Each of Compositions 31 and 32 showed significant inhibitory effects of CNV, as compared to DMSO and SB225002.

TABLE 5

|  | mean | S.E. | n | Test results |
| --- | --- | --- | --- | --- |
| DMSO | 42892 | 2424 | 10 |  |
| SB225002 | 43121 | 1836 | 9 | N.S. |
| Composition 31 | 34453 | 2664 | 10 | *, # |
| Composition 32 | 33387 | 3009 | 10 | *, # |

* $P < 0.05$ (vs. DMSO), t-test
: $P < 0.05$ (vs. SB225002), t-test
N.S.: Not Significant (vs. DMSO), t-test ⟨Conclusions⟩
The composition comprising SB225002 and Gel-One was shown to be able to be used as a drug for treating a posterior eye disease, especially AMD, which exhibited medicinal effects higher than those of SB225002. The crosslinked GAG was shown to be able to be used as the GAG derivative, and HA was shown to be able to be used as GAG. Further, SB225002 was shown to be able to be used as a chemokine receptor antagonist.

(Test Example 6) Assay of CNV Inhibitory Effects Using a Composition Comprising GW766994 and Crosslinked HA (Gel-One)

Figure 6:
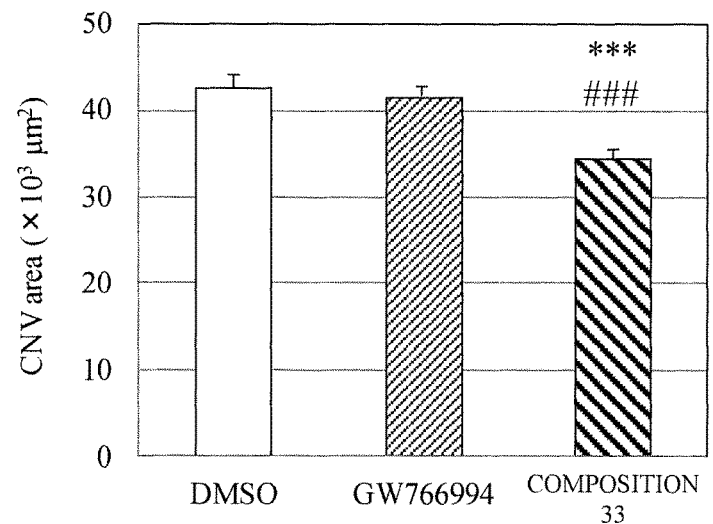
FIG. 6 is a graph illustrating CNV inhibitory effects of the composition of the present embodiment comprising GW766994 and an HA derivative, the composition intravitreally administered to an animal model.

Laser-induced CNV models of rat were prepared, and neovascularization inhibitory effect was examined with respect to intravitreal administration of a composition comprising GW766994 and Gel-One (photocrosslinked HA: manufactured by SEIKAGAKU CORPORATION) as well as GW766994.
⟨Test Substances⟩
GW766994 was dissolved in DMSO to obtain a solution of GW766994 (2 mg/mL). GW766994 was dissolved in DMSO to obtain a solution of GW766994 (50 mg/mL), and the resultant 50 mg/mL solution of GW766994 (0.0417 mL) was mixed with Gel-One (1.0 mL) and stirred to thereby obtain Composition 33. The following test substances were used in the assay.
1) Composition 33 (containing 2 mg/mL of GW766994)
2) GW766994 (2 mg/mL)
3) DMSO
⟨Method⟩
Substantially the same procedure as in ⟨Method⟩ for Test Example 1 was repeated.
⟨Statistical Analysis⟩
The areas of CNV in each group were analyzed by a test (t-test) for unpaired two groups. The significance level was 5% on both sides.
⟨Results of Assay⟩
The results of measurement of the CNV area are given in the table below and FIG. 6.
Composition 33 showed significant inhibitory effects of CNV, as compared to DMSO and GW766994.

TABLE 6

|  | mean | S.E. | n | Test results |
| --- | --- | --- | --- | --- |
| DMSO | 42613 | 1404 | 9 |  |
| GW766994 | 41548 | 1258 | 9 | N.S. |
| Composition 33 | 34476 | 1052 | 10 | ***, ### |

*** $P < 0.001$ (vs. DMSO), t-test
: $P < 0.001$ (vs. GW766994), t-test
N.S.: Not Significant (vs. DMSO), t-test ⟨Conclusions⟩
The composition comprising GW766994 and Gel-One was shown to be able to be used as a drug for treating a posterior eye disease, especially AMD, which exhibited medicinal effects higher than those of GW766994. Further, GW766994 was shown to be able to be used as a chemokine receptor antagonist.

(Test Example 7) Assay of CNV Inhibitory Effects Using a Composition Comprising Ki19003 and Crosslinked HA (Gel-One)

Figure 7:
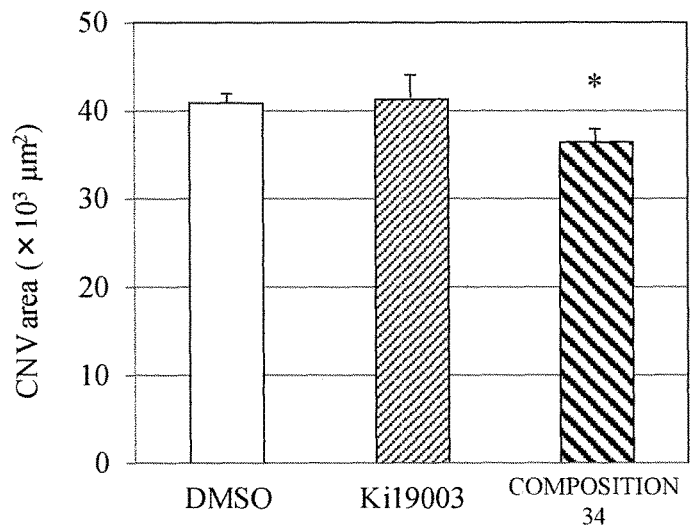
FIG. 7 is a graph illustrating CNV inhibitory effects of the composition of the present embodiment comprising Ki19003 and an HA derivative, the composition intravitreally administered to an animal model.

Laser-induced CNV models of rat were prepared, and neovascularization inhibitory effect was examined with respect to intravitreal administration of a composition comprising Ki19003 and Gel-One (photocrosslinked HA: manufactured by SEIKAGAKU CORPORATION) as well as Ki19003.
⟨Test Substances⟩
Ki19003 was dissolved in DMSO to obtain a solution of Ki19003 (0.5 mg/mL). Ki19003 was dissolved in DMSO to obtain a solution of Ki19003 (25 mg/mL), and the resultant 25 mg/mL solution of Ki19003 (0.0204 mL) was mixed with Gel-One (1.0 mL) and stirred to thereby obtain Composition 34. The following test substances were used in the assay.
1) Composition 34 (containing 0.5 mg/mL of Ki19003)
2) Ki19003 (0.5 mg/ml)
3) DMSO
⟨Method⟩
Substantially the same procedure as in ⟨Method⟩ for Test Example 1 was repeated.
⟨Statistical Analysis⟩
The areas of CNV in each group were analyzed by a test (t-test) for unpaired two groups. The significance level was 5% on both sides.
⟨Results of Assay⟩
The results of measurement of the CNV area are given in the table below and FIG. 7.
Composition 34 showed significant inhibitory effects of CNV, as compared to DMSO.

TABLE 7

|  | mean | S.E. | n | Test results |
| --- | --- | --- | --- | --- |
| DMSO | 40833 | 1147 | 10 |  |
| Ki19003 | 41393 | 2614 | 10 | N.S. |
| Composition 34 | 36423 | 1483 | 10 | * |

* $P < 0.05$ (vs. DMSO), t-test
N.S.: Not Significant (vs. DMSO), t-test

⟨Conclusions⟩
The composition comprising Ki19003 and Gel-One was shown to be able to be used as a drug for treating a posterior eye disease, especially AMD, which exhibited medicinal effects higher than those of Ki19003. Test Examples 1, 2, 3 and 7 showed that a plurality of types of GAG derivatives (hydrophobic group-introduced GAG or crosslinked GAG) could be used in combination with Ki19003. This fact showed that the GAG derivative and chemokine receptor antagonist which might be used in combination were not always in one-to-one correspondence.

(Test Example 8) Assay of CNV Inhibitory Effects Using a Composition Comprising AZD3778 and Crosslinked HA (Gel-One)

Laser-induced CNV models of rat were prepared, and neovascularization inhibitory effect was examined with respect to intravitreal administration of a composition comprising AZD3778 (synthesized in accordance with WO 03/004487 A1) and Gel-One (photocrosslinked HA: manufactured by SEIKAGAKU CORPORATION) as well as AZD3778.

⟨Test Substances⟩

AZD3778 was dissolved in DMSO to obtain a solution of AZD3778 (0.1 mg/mL). AZD3778 was dissolved in DMSO to obtain a solution of AZD3778 (5 mg/mL), and the resultant 5 mg/mL solution of AZD3778 (0.0204 mL) was mixed with Gel-One (1.0 mL) and stirred to thereby obtain Composition 35. The following test substances were used in the assay.
1) Composition 35 (containing 0.1 mg/mL of AZD3778)
2) AZD3778 (0.1 mg/ml)
3) DMSO ⟨Method⟩

Substantially the same procedure as in ⟨Method⟩ for Test Example 1 was repeated.

⟨Statistical Analysis⟩

The areas of CNV in each group were analyzed by a test (t-test) for unpaired two groups. The significance level was 5% on both sides.

⟨Results of Assay⟩

Figure 8:
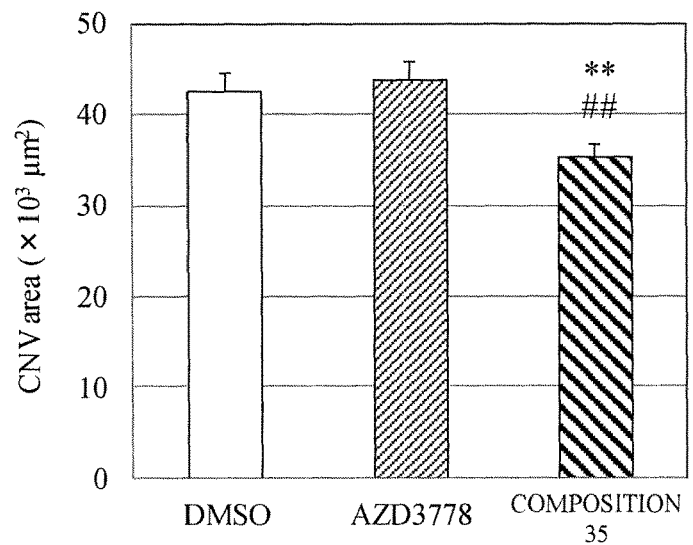
FIG. 8 is a graph illustrating CNV inhibitory effects of the composition of the present embodiment comprising AZD3778 and an HA derivative, the composition intravitreally administered to an animal model.

The results of measurement of the CNV area are given in the table below and FIG. 8.

Composition 35 showed significant inhibitory effects of CNV, as compared to AZD3778.

TABLE 8

|  | mean | S.E. | n | Test results |
|---|---|---|---|---|
| DMSO | 42579 | 2016 | 10 |  |
| AZD3778 | 43935 | 1952 | 10 | N.S. |
| Composition 35 | 35345 | 1441 | 10 | **, ## |

** P < 0.01 (vs. DMSO), t-test
: P < 0.01 (vs. AZD3778), t-test
N.S.: Not Significant (vs. DMSO), t-test ⟨Conclusions⟩

The composition comprising AZD3778 and Gel-One was shown to be able to be used as a drug for treating a posterior eye disease, especially AMD, which exhibited medicinal effects higher than those of AZD3778. Further, AZD3778 was shown to be able to be used as a chemokine receptor antagonist.

(Test Example 9) Assay of CNV Inhibitory Effects Using a Composition Comprising SB328437 and Crosslinked HA (Gel-One)

Laser-induced CNV models of rat were prepared, and neovascularization inhibitory effect was examined with respect to intravitreal administration of a composition comprising SB328437 and Gel-One (photocrosslinked HA: manufactured by SEIKAGAKU CORPORATION) as well as SB328437.

⟨Test Substances⟩

SB328437 was dissolved in DMSO to obtain a solution of SB328437 (1 mg/mL). SB328437 was dissolved in DMSO to obtain a solution of SB328437 (50 mg/mL), and the resultant 50 mg/mL solution of SB328437 (0.02 mL) was mixed with Gel-One (1.0 mL) and stirred to thereby obtain Composition 36. The following test substances were used in the assay.
1) Composition 36 (containing 1 mg/mL of SB328437)
2) SB328437 (1 mg/ml)
3) DMSO ⟨Method⟩

Substantially the same procedure as in ⟨Method⟩ for Test Example 1 was repeated.

⟨Statistical Analysis⟩

The areas of CNV in each group were analyzed by a test (t-test) for unpaired two groups. The significance level was 5% on both sides.

⟨Results of Assay⟩

Figure 9:
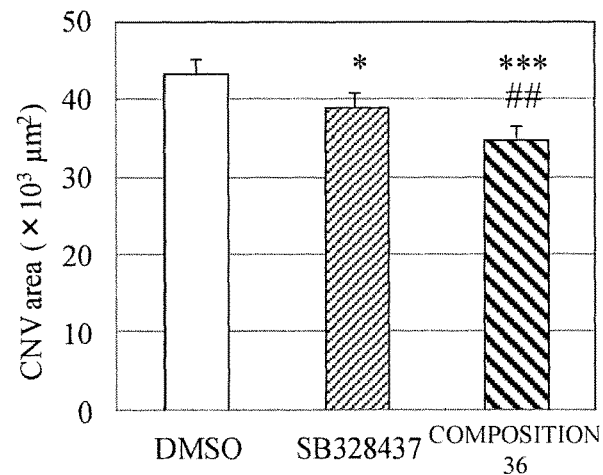
FIG. 9 is a graph illustrating CNV inhibitory effects of the composition of the present embodiment comprising SB328437 and an HA derivative, the composition intravitreally administered to an animal model.

The results of measurement of the CNV area are given in the table below and FIG. 9.

Composition 36 showed significant inhibitory effects of CNV, as compared to SB328437.

TABLE 9

|  | mean | S.E. | n | Test results |
|---|---|---|---|---|
| DMSO | 43155 | 1548 | 10 |  |
| SB328437 | 38911 | 988 | 10 | * |
| Composition 36 | 35012 | 751 | 10 | ***, ## |

* P < 0.05,
*** P < 0.001 (vs. DMSO), t-test
: P < 0.01 (vs. SB328437), t-test ⟨Conclusions⟩

The composition comprising SB328437 and Gel-One was shown to be able to be used as a drug for treating a posterior eye disease, especially AMD, which exhibited medicinal effects higher than those of SB328437. Further, SB328437 was shown to be able to be used as a chemokine receptor antagonist. Test Examples 5, 6, 7, 8 and 9 showed that a plurality of types of chemokine receptor antagonists (GW766994, Ki19003, AZD3778, SB328437 and SB225002) could be used in combination with the crosslinked GAG. This fact showed that the GAG derivative and chemokine receptor antagonist which might be used in combination were not always in one-to-one correspondence.

(Test Example 10) Assay of CNV Inhibitory Effects Using Compositions 6 and 7

Laser-induced CNV models of rat were prepared, and neovascularization inhibitory effect was examined with respect to intravitreal administration of each of Compositions 6, 7 and GW766994.

(⟨Test Substances⟩

GW766994 was dissolved in DMSO to obtain a solution of GW766994 (1.5 mg/mL). The following test substances were used in the assay.
1) Composition 6 (containing 0.71 mg/mL of GW766994)
2) Composition 7 (containing 0.83 mg/mL of GW766994)
3) GW766994 (1.5 mg/mL)
4) DMSO
(The samples for administration to animals prepared in Examples 6 and 7 were used as Compositions 6 and 7, respectively.)

⟨Method⟩

Substantially the same procedure as in ⟨Method⟩ for Test Example 1 was repeated.

⟨Statistical Analysis⟩

The areas of CNV in the DMSO group and other groups were analyzed by Dunnett's test. The significance level was 5% on both sides. The areas of CNV in the GW766994 group and other Compositions groups were analyzed by Dunnett's test. The significance level was 5% on both sides.

⟨Results of Assay⟩

Figure 10:
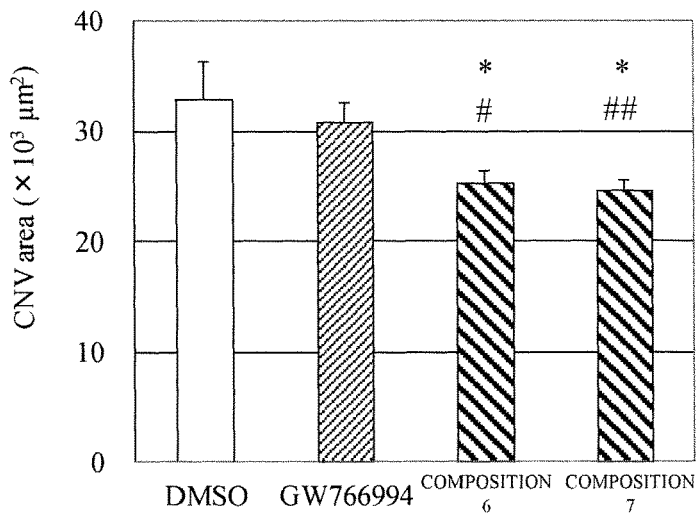
FIG. 10 is a graph illustrating CNV inhibitory effects of the composition of the present embodiment comprising GW766994 and a GAG derivative, the composition intravitreally administered to an animal model.

The results of measurement of the CNV area are given in the table below and FIG. 10.

Each of Compositions 6 and 7 showed significant inhibitory effects of CNV, as compared to GW766994.

TABLE 10

|  | mean | S.E. | n | Test results |
|---|---|---|---|---|
| DMSO | 32889 | 3371 | 8 |  |
| GW766994 | 30795 | 1701 | 8 | N.S. |
| Composition 6 | 25387 | 1010 | 7 | *, # |
| Composition 7 | 24614 | 969 | 8 | *, ## |

* P < 0.05 (vs. DMSO), Dunnett's test
N.S.: Not Significant (vs. DMSO), Dunnett's test
: P < 0.05, ##: P < 0.01 (vs. GW766994), Dunnett's test ⟨Conclusions⟩

Each of the composition comprising GW766994 and hydrophobic group-introduced HA and the composition comprising GW766994 and hydrophobic group-introduced CS was shown to be able to be used as a drug for treating a posterior eye disease, especially AMD, which exhibited medicinal effects higher than those of GW766994. Further, each of HA and CS was shown to be able to be used as GAG to constitute the hydrophobic group-introduced GAG.

(Test Example 11) Assay of CNV Inhibitory Effects Using Compositions 4 and 5

Laser-induced CNV models of rat were prepared, and neovascularization inhibitory effect was examined with respect to intravitreal administration of Compositions 4, 5 and Ki19003.

⟨Test Substances⟩

Ki19003 was dissolved in DMSO to obtain a solution of Ki19003 (0.6 mg/mL).

The following test substances were used in the assay.
1) Composition 4 (containing 0.42 mg/mL of Ki19003)
2) Composition 5 (containing 0.66 mg/mL of Ki19003)
3) Ki19003 (0.6 mg/mL)
4) DMSO
(The samples for administration to animals prepared in Examples 4 and 5 were used as Compositions 4 and 5, respectively.)

⟨Method⟩

Substantially the same procedure as in ⟨Method⟩ for Test Example 1 was repeated.

⟨Statistical Analysis⟩

The areas of CNV in the DMSO group and other groups were analyzed by Dunnett's test. The significance level was 5% on both sides.

⟨Results of Assay⟩

Figure 11:
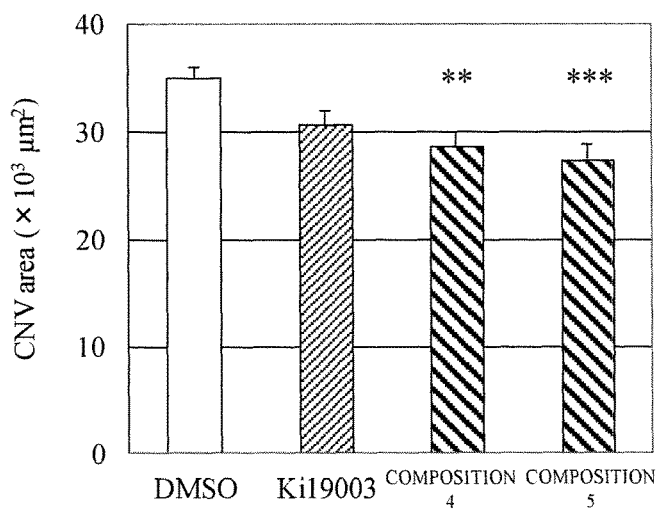
FIG. 11 is a graph illustrating CNV inhibitory effects of the composition of the present embodiment comprising Ki19003 and a GAG derivative, the composition intravitreally administered to an animal model.

The results of measurement of the CNV area are given in the table below and FIG. 11. Each of Compositions 4 and 5 showed significant inhibitory effects of CNV, as compared to DMSO.

TABLE 11

|  | mean | S.E. | n | Test results |
|---|---|---|---|---|
| DMSO | 34980 | 1125 | 16 |  |
| Ki19003 | 30752 | 1371 | 14 | N.S. |
| Composition 4 | 28766 | 1226 | 13 | ** |
| Composition 5 | 27525 | 1346 | 15 | *** |

** P < 0.01,
*** P < 0.001 (vs. DMSO), Dunnett's test
N.S.: Not Significant (vs. DMSO), Dunnett's test ⟨Conclusions⟩

Each of the composition comprising Ki19003 and hydrophobic group-introduced HA and the composition comprising Ki19003 and hydrophobic group-introduced CS was shown to be able to be used as a drug for treating a posterior eye disease, especially AMD, which exhibited medicinal effects higher than those of Ki19003. Further, each of HA and CS was shown to be able to be used as GAG to constitute the hydrophobic group-introduced GAG.

(Test Example 12) Assay of CNV Inhibitory Effects and Influence on Intraocular Hemorrhage Using Composition 8

Laser-induced CNV models of rat were prepared, and neovascularization inhibitory effect and influence on intraocular hemorrhage were examined with respect to intravitreal administration of Composition 8 or a formulation comprising heparin and GW766994.

⟨Test Substances⟩

GW766994 was dissolved in DMSO to obtain a solution of GW766994 (10 mg/mL). Heparin (10 mg, manufactured by Aldrich) was dissolved in PBS (1 mL) to obtain a heparin solution (10 mg/mL). The heparin solution and 10 mg/mL solution of GW766994 (0.1 mL) were mixed to thereby obtain Formulation 2 comprising heparin and GW766994. The following test substances were used in the assay.
1) Composition 8 (containing 0.96 mg/mL of GW766994)
2) Formulation 2 (containing 0.91 mg/mL of GW766994)
3) PBS
(The sample for administration to animals prepared in Example 8 was used as Composition 8.)

⟨Method⟩

(Neovascularization Inhibitory Effects)

Substantially the same procedure as in ⟨Method⟩ for Test Example 1 was repeated.

(Influence on Intraocular Hemorrhage)

Immediately after the administration of the test substance and after 10 days from the administration, intraocular hemorrhage was evaluated by scoring, and the influence on intraocular hemorrhage was examined based on the presence or absence of worsening of intraocular hemorrhage.

(1) Evaluation of Intraocular Hemorrhage by Scoring Immediately after the Administration of the Test Substance Intraocular observation was carried out using a slit lamp and the like, and the intraocular hemorrhage was scored in accordance with the following criteria of intraocular hemorrhage for scoring.

Score 0: No hemorrhage was observed in the observed area.
Score 1: The area with observed hemorrhage was ¼ or less of the observed area.
Score 2: The area with observed hemorrhage was ¼ or more and ½ or less of the observed area.
Score 3: The area with observed hemorrhage was ½ or more of the observed area.

(2) Evaluation of Intraocular Hemorrhage by Scoring 10 Days after the Administration Immediately after the preparation of the eye cup, the vitreous humor and retina were observed and hemorrhage in each of the vitreous humor and retina was scored in accordance with the following criteria of hemorrhage in the vitreous humor and retina for scoring. The average value of the scores of hemorrhage in the vitreous humor and that in the retina was obtained as the score of intraocular hemorrhage.

Score 0: No hemorrhage was observed in the observed area.
Score 1: The area with observed hemorrhage was ¼ or less of the observed area.
Score 2: The area with observed hemorrhage was ¼ or more and ½ or less of the observed area.
Score 3: The area with observed hemorrhage was ½ or more of the observed area.

(3) Calculation of the Presence or Absence of Worsening of Intraocular Hemorrhage The differences in score of intraocular hemorrhage after 10 days from the administration of the test substance relative to that immediately after the administration and that were calculated and, based on these differences, the numbers of eyes with (the difference was positive)/without (the difference was negative or 0) worsening of hemorrhage were determined.

⟨Statistical Analysis⟩

The areas of CNV in each group were analyzed by a test (t-test) for unpaired two groups. The significance level was 5% on both sides.

The presence or absence of worsening of intraocular hemorrhage in each group was analyzed by 2×2 Fisher's exact test. The significance level was 5% on one side.

⟨Results of Assay⟩

Figure 12:
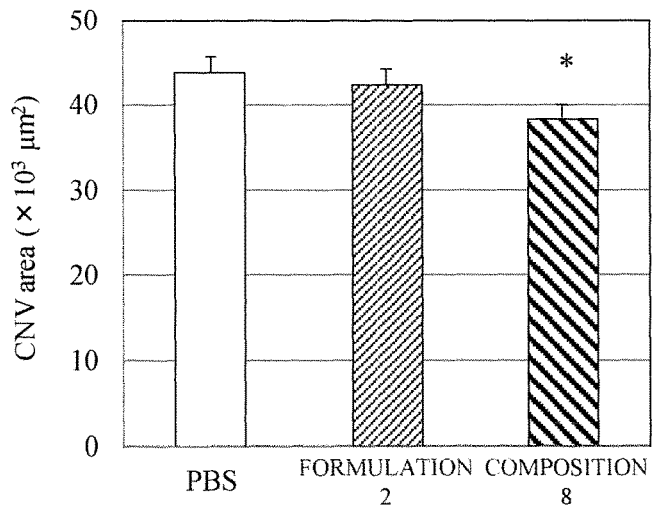
FIG. 12 is a graph illustrating CNV inhibitory effects of the composition of the present embodiment comprising GW766994 and a CS derivative, the composition intravitreally administered to an animal model.

The results of measurement of the CNV area are given in Table 12 below and FIG. 12. Composition 8 showed significant inhibitory effects of CNV, as compared to PBS.

The results of examination of the influence on intraocular hemorrhage are given in Table 13. The number of eyes with worsening of intraocular hemorrhage for Formulation 2 comprising heparin and GW766994 was shown to be significantly large, as compared to that for each of PBS and Composition 8.

TABLE 12

|  | mean | S.E. | n | Test results |
|---|---|---|---|---|
| PBS | 43914 | 1824 | 14 |  |
| Formulation 2 | 42506 | 1710 | 20 | N.S. |
| Composition 8 | 38469 | 1454 | 18 | * |

* P < 0.05 (vs. PBS), t-test
N.S.: Not Significant (vs. PBS), t-test

TABLE 13

| Test substances | Worsening of intraocular bleeding | | Number of eyes | |
|---|---|---|---|---|
|  | Absent | Present | examined | Test results |
| PBS | 13 | 1 | 14 |  |
| Formulation 2 | 12 | 8 | 20 | *, # |
| Composition 8 | 16 | 2 | 18 | N.S. |

* P < 0.05 (vs. PBS)
: P < 0.05 (vs. Composition 8)
N.S.: Not Significant (vs. PBS)

⟨Conclusions⟩

The composition comprising GW766994 and hydrophobic group-introduced CS was shown to be able to be used as a drug for treating a posterior eye disease, especially AMD, which exhibited medicinal effects higher than those of Formulation 2 comprising heparin and GW766994. It was also shown that a mere blend of GAG and a chemokine receptor antagonist is not satisfactory as a drug for treating a posterior eye disease, and the usefulness of a composition comprising the GAG derivative and chemokine receptor antagonist was thus confirmed.

In view of occurrence of worsening of intraocular hemorrhage, Formulation 2 comprising heparin and GW766994 was shown to be unsuitable for intravitreal administration.

(Test Example 13) Assay of Degeneration of Tissues Caused by Intravitreal Administration of a Chemokine Receptor Antagonist Solution Used in Patent Literature 1, which Contains a Solubilizing Agent (DMSO), as Well as the Composition of the Present Invention Test substances were intravitreally administered once to rats, and the intraocular conditions were observed.

⟨Test Substances⟩

The following test substances were used in the assay.
1) Ki19003 (0.6 mg/mL)
2) SB328437 (1 mg/mL)
3) GW766994 (1.5 mg/mL)
4) Composition 5 (containing 0.66 mg/mL of Ki19003)
5) Composition 7 (containing 0.83 mg/mL of GW766994)
6) Composition 10 (containing 0.54 mg/mL of Ki19003)
7) Composition 11 (containing 0.53 mg/mL of Ki19003)
8) Composition 36 (containing 1 mg/mL of SB328437)
(The samples for administration to animals prepared in Examples 5, 7, 10 and 11 and Test Example 9 were used as Composition 5, 7, 10, 11 and 36, respectively.)

Solutions of Ki19003, SB328437 and GW766994 were obtained in substantially the same manner as in Test Examples 1, 9 and 10, respectively.

⟨Method⟩
(1) Administration of Test Substances

BN/CrlCrlj rats (male, CHARLES RIVER LABORATORIES JAPAN, INC.) were used as an animal for this assay. Under general anesthesia by intraperitoneal administration of an anesthetic mixture (saline:Somnopentyl=9:1) (about 2 mL/body), Mydrin-P ophthalmic solution was topically instilled to cause mydriasis in both eyes. Thereafter, 5 µL/eye of the test substance was administered once into the vitreous bodies of both eyes. Immediately after the administration, one drop of an antimicrobial drug (VEGAMOX Ophthalmic Solution 0.5%) was instilled.

(2) Intraocular Imaging

Photographs of the conditions of inside of eyes of the rats were taken with a digital microscope.

⟨Results of Assay⟩

The results of the intraocular imaging are shown in FIGS. 18A to 18H.

As pointed out with an arrow in the figures, each of the chemokine receptor antagonist solutions (Ki19003 (FIG. 18A), SB328437 (FIG. 18B) and GW766994 (FIG. 18C)) containing a solubilizing agent caused degeneration of the lenticular tissue. In contrast, with respect to Composition 5 (FIG. 18D), Composition 7 (FIG. 18E), Composition 10 (FIG. 18F), Composition 11 (FIG. 18G) and Composition 36 (FIG. 18H), each of which is a composition comprising the GAG derivative and chemokine receptor antagonist, no degeneration of the lenticular tissue was observed.

⟨Summary⟩

The composition comprising the GAG derivative and chemokine receptor antagonist was shown to exhibit excellent antagonistic activity against a chemokine receptor, as compared to a chemokine receptor antagonist solution containing a solubilizing agent, while suppressing occurrence of rapid degeneration of tissues.

(Test Example 14) Assay of CNV Inhibitory Effects Using a Composition Comprising RS504393 and Crosslinked HA (Gel-One)

Laser-induced CNV models of rat were prepared, and neovascularization inhibitory effect was examined with respect to intravitreal administration of each of a composition comprising RS504393 and Gel-One (photocrosslinked HA: manufactured by SEIKAGAKU CORPORATION) as well as RS504393.

⟨Test Substances⟩
RS504393 (10 mg, manufactured by Abcam) was dissolved in DMSO to obtain a solution of RS504393 (0.01 mg/mL). RS504393 was dissolved in DMSO to obtain a solution of RS504393 (1 mg/mL), and the resultant 1 mg/mL solution of RS504393 (0.01 mL) was mixed with Gel-One (1.0 mL) and stirred to thereby obtain Composition 37. The following test substances were used in the assay.
1) Composition 37 (containing 0.01 mg/mL of RS504393)
2) RS504393 (0.01 mg/ml)
3) DMSO ⟨Method⟩
Substantially the same procedure as in ⟨Method⟩ for Test Example 1 was repeated.

⟨Statistical Analysis⟩
The areas of CNV in each group were analyzed by a test (t-test) for unpaired two groups. The significance level was 5% on both sides.

Figure 13:
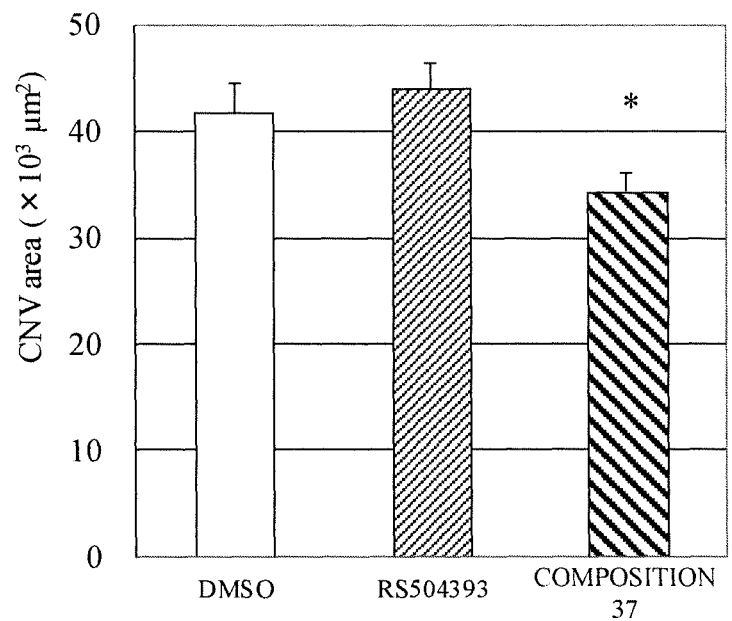
FIG. 13 is a graph illustrating CNV inhibitory effects of the composition of the present embodiment comprising RS504393 and an HA derivative, the composition intravitreally administered to an animal model.

⟨Results of Assay⟩
The results of measurement of the CNV area are given in the table below and FIG. 13.

Composition 37 showed significant inhibitory effects of CNV, as compared to DMSO and RS504393.

TABLE 14

|  | mean | S.E. | n | Test results |
|---|---|---|---|---|
| DMSO | 41672 | 2812 | 10 |  |
| RS504393 | 44137 | 2231 | 10 | N.S. |
| Composition 37 | 34418 | 1624 | 10 | *, ## |

* P < 0.05 (vs. DMSO), t-test
: P < 0.01 (vs. RS504393), t-test
N.S.: Not Significant (vs. DMSO), t-test ⟨Conclusions⟩
The composition comprising RS504393 and Gel-One was shown to be able to be used as a drug for treating a posterior eye disease, especially AMD, which exhibited medicinal effects higher than those of RS504393. Further, RS504393 was shown to be able to be used as a chemokine receptor antagonist.

(Test Example 15) Assay of CNV Inhibitory Effects Using a Composition Comprising PS372424 and Crosslinked HA (Gel-One)

Laser-induced CNV models of rat were prepared, and neovascularization inhibitory effect was examined with respect to intravitreal administration of a composition comprising PS372424 and Gel-One (photocrosslinked HA: manufactured by SEIKAGAKU CORPORATION) as well as PS372424.

⟨Test Substances⟩
PS372424 (10 mg, manufactured by Calbiochem) was dissolved in DMSO to obtain a solution of PS372424 (0.1 mg/mL). PS372424 was dissolved in DMSO to obtain a solution of PS372424 (1 mg/mL), and the resultant 1 mg/mL solution of PS372424 (0.1 mL) was mixed with Gel-One (1.0 mL) and stirred to thereby obtain Composition 38. The following test substances were used in the assay.
1) Composition 38 (containing 0.091 mg/mL of PS372424)
2) PS372424 (0.1 mg/ml)
3) DMSO ⟨Method⟩
Substantially the same procedure as in ⟨Method⟩ for Test Example 1 was repeated.

⟨Statistical Analysis⟩
The areas of CNV in each group were analyzed by a test (t-test) for unpaired two groups. The significance level was 5% on both sides.

Figure 14:
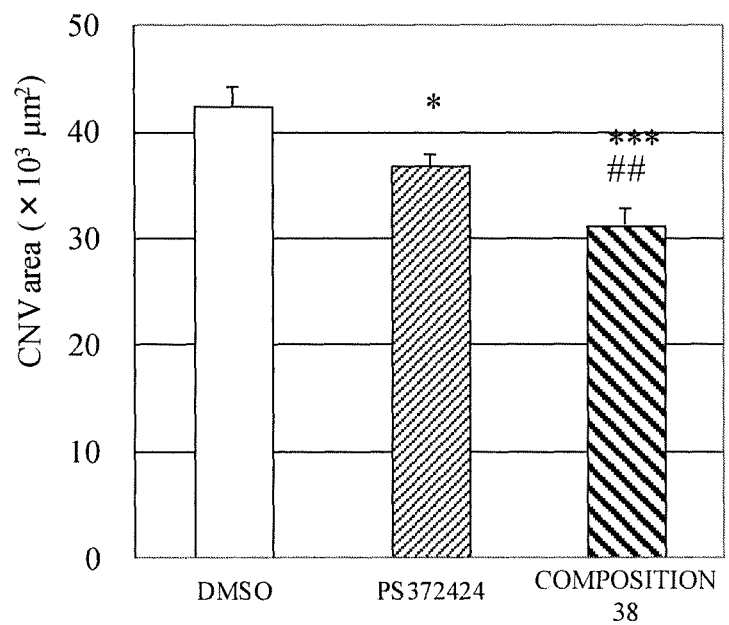
FIG. 14 is a graph illustrating CNV inhibitory effects of the composition of the present embodiment comprising PS372424 and an HA derivative, the composition derivative intravitreally administered to an animal model.

⟨Results of Assay⟩
The results of measurement of the CNV area are given in the table below and FIG. 14.

Composition 38 showed significant inhibitory effects of CNV, as compared to DMSO and PS372424.

TABLE 15

|  | mean | S.E. | n | Test results |
|---|---|---|---|---|
| DMSO | 42437 | 1873 | 9 |  |
| PS372424 | 36842 | 1023 | 10 | * |
| Composition 38 | 31285 | 1553 | 10 | ***, ## |

* P < 0.05 (vs. DMSO), t-test
*** P < 0.001 (vs. DMSO), t-test
: P < 0.01 (vs. PS372424), t-test ⟨Conclusions⟩
The composition comprising PS372424 and Gel-One was shown to be able to be used as a drug for treating a posterior eye disease, especially AMD, which exhibited medicinal effects higher than those of PS372424. Further, PS372424 was shown to be able to be used as a chemokine receptor agonist.

(Test Example 16) Assay of CNV Inhibitory Effects Using Composition 22 (Lithocholic Acid-Introduced CS: Example 22) and Composition 19 (Oleic Acid-Introduced CS: Example 19)

Laser-induced CNV models of rat were prepared, and neovascularization inhibitory effect was examined with respect to intravitreal administration of Compositions 22 and 19.

⟨Test Substances⟩
The following test substances were used in the assay.
1) PBS
2) Composition 22 (containing 0.86 mg/mL of GW766994)
3) Composition 19 (containing 1.03 mg/mL of GW766994)
(The samples for administration to animals prepared in Examples 22 and 19 were used as Compositions 22 and 19, respectively.)

⟨Method⟩
Substantially the same procedure as in ⟨Method⟩ for Test Example 1 was repeated.

⟨Statistical Analysis⟩
The areas of CNV in the PBS group and other groups were analyzed by a test (t-test) for unpaired two groups. The significance level was 5% on both sides.

Figure 15:
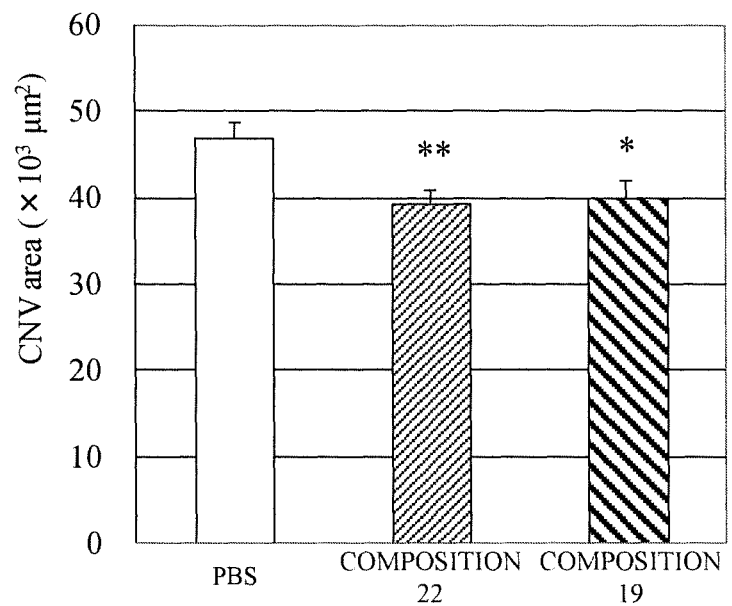
FIG. 15 is a graph illustrating CNV inhibitory effects of the composition of the present embodiment comprising GW766994 and a CS derivative, the composition intravitreally administered to an animal model.

⟨Results of Assay⟩
The results of measurement of the CNV area are given in the table below and FIG. 15. Each of Compositions 22 and 19 showed significant inhibitory effects of CNV, as compared to PBS.

TABLE 16

|  | mean | S.E. | n | Test results |
|---|---|---|---|---|
| PBS | 46885 | 1877 | 10 |  |
| Composition 22 | 39428 | 1423 | 10 | ** |
| Composition 19 | 39917 | 1987 | 10 | * |

* $P < 0.05$ (vs. PBS), t-test
** $P < 0.01$ (vs. PBS), t-test

As described in Test Examples 6 and 10, GW766994 dissolved in DMSO (2 mg/mL and 1.5 mg/mL) did not have inhibitory effects of CNV, at both concentrations, as compared to DMSO.

⟨Conclusions⟩

The composition comprising GW766994 and hydrophobic group-introduced CS was shown to be able to be used as a drug for treating a posterior eye disease, especially AMD, which exhibited medicinal effects higher than those of GW766994. Further, as the "hydrophobic group" in the hydrophobic group-introduced GAG, a group derived from an alicyclic compound, such as cholanic acid (the basic skeleton of bile acids, such as lithocholic acid), and a group derived from a fatty acid, such as oleic acid, were shown to be able to be used.

(Test Example 17) Assay of Degeneration of Tissues Caused by Intravitreal Administration of a Chemokine Receptor Activity Regulator Solution Used in U.S. Pat. No. 8,592,482, which Contains a Solubilizing Agent (DMSO), as Well as the Composition of the Present Invention Test substances were intravitreally administered once to rats, and the intraocular conditions were observed.

⟨Test Substances⟩

The following test substances were used in the assay.
1) RS504393 (0.01 mg/mL)
2) PS372424 (0.1 mg/mL)
3) Composition 37 (containing 0.01 mg/mL of RS504393)
4) Composition 38 (containing 0.1 mg/mL of PS372424)
5) Composition 22 (containing 0.86 mg/mL of GW766994)
6) Composition 19 (containing 1.03 mg/mL of GW766994)
(The samples for administration to animals prepared in Examples 14 (Composition 37 and RS504393) and 15 (Composition 38 and PS372424) and 22 (Composition 22) and 19 (Composition 19) were used as Composition 37, RS504393, Composition 38, PS372424, Composition 22 and Composition 19, respectively.)

⟨Method⟩

Substantially the same procedure as in ⟨Method⟩ for Test Example 13 was repeated.

⟨Results of Assay⟩

The results of the intraocular imaging are shown in FIGS. 19A to 19F.

As pointed out with an arrow in the figures, each of the chemokine receptor activity regulator solutions (RS504393 (FIG. 19A) and PS372424 (FIG. 19B)) containing a solubilizing agent caused degeneration of the lenticular tissue. In contrast, with respect to Composition 37 (FIG. 19C), Composition 38 (FIG. 19D), Composition 22 (FIG. 19E) and Composition 19 (FIG. 19F), each of which is a composition comprising the GAG derivative and chemokine receptor activity regulator, no degeneration of the lenticular tissue was observed.

⟨Summary⟩

The composition comprising the GAG derivative and chemokine receptor activity regulator was shown to exhibit excellent regulatory activity against a chemokine receptor, as compared to a chemokine receptor activity regulator solution containing a solubilizing agent, while suppressing occurrence of rapid degeneration of tissues.

(Test Example 18) Assay of CNV Inhibitory Effects Using CS

Laser-induced CNV models of rat were prepared, and neovascularization inhibitory effect was examined with respect to intravitreal administration of CS.

⟨Test Substances⟩

CS (average molecular weight: about 140,000, manufactured by SEIKAGAKU CORPORATION) was dissolved in PBS to obtain a CS solution (20 mg/mL). The following test substances were used in the assay.
1) CS (20 mg/mL)
2) PBS ⟨Method⟩

Substantially the same procedure as in ⟨Method⟩ for Test Example 1 was repeated.

⟨Statistical Analysis⟩

The areas of CNV in each group were analyzed by a test (t-test) for unpaired two groups. The significance level was 5% on both sides.

⟨Results of Assay⟩

Figure 16:
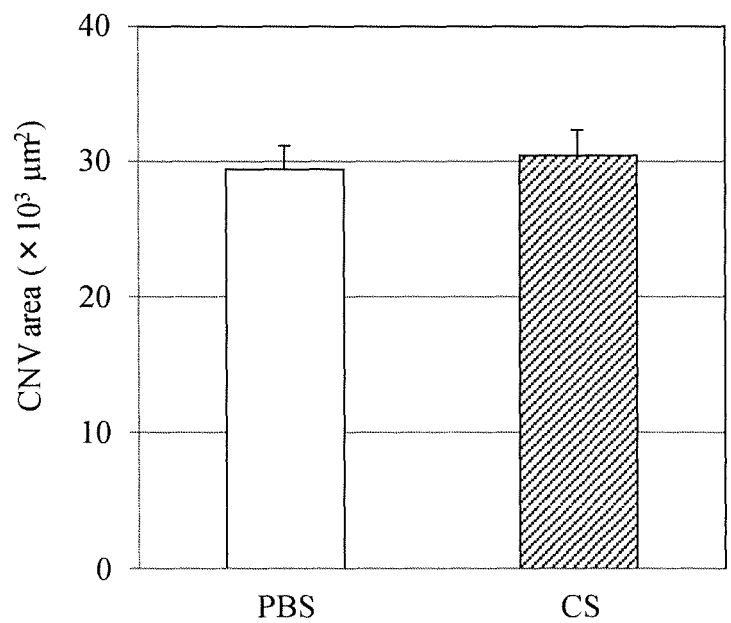
FIG. 16 is a graph in which CNV inhibitory effects of CS intravitreally administered to an animal model are confirmed.

The results of measurement of the CNV area are given in the table below and FIG. 16.

CS did not show significant inhibitory effects of CNV, as compared to PBS.

TABLE 17

|  | mean | S.E. | n | Test results |
|---|---|---|---|---|
| PBS | 29359 | 1743 | 10 |  |
| CS | 30462 | 1865 | 8 | N.S. |

N.S.: Not Significant (vs. PBS), t-test

Administration of CS alone did not show significant medicinal effects as a drug for treating age-related macular degeneration.

(Test Example 19) Assay of CNV Inhibitory Effects Using Compound 3

Laser-induced CNV models of rat were prepared, and neovascularization inhibitory effect was examined with respect to intravitreal administration of Compound 3.

⟨Test Substances⟩

CS (average molecular weight: about 40,000, manufactured by SEIKAGAKU CORPORATION) was dissolved in PBS to obtain a CS solution (10 mg/mL). The following test substances were used in the assay.
1) Compound 3
2) CS (10 mg/mL)

⟨Method⟩

Substantially the same procedure as in ⟨Method⟩ for Test Example 1 was repeated, except that flat mounts were prepared 4 days after the preparation of models, instead of 10 days after the preparation of models in Test Example 1.

⟨Statistical Analysis⟩

The areas of CNV in each group were analyzed by a test (t-test) for unpaired two groups. The significance level was 5% on both sides.

⟨Results of Assay⟩

Figure 17:
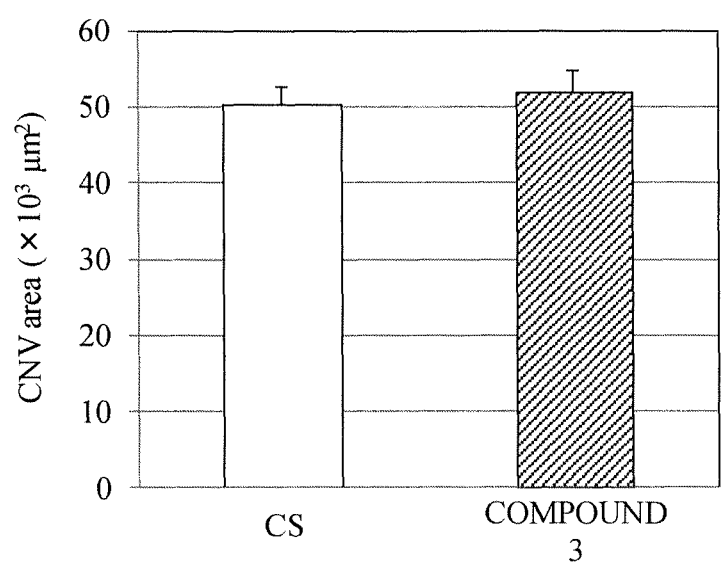
FIG. 17 is a graph in which CNV inhibitory effects of CS or a CS derivative intravitreally administered to an animal model are confirmed.
Figure 18A:
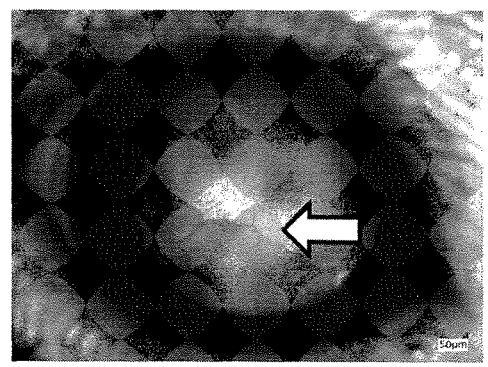
FIG. 18A is an image showing the intraocular conditions after the intravitreal administration of a Ki19003 solution to an animal.
Figure 18B:
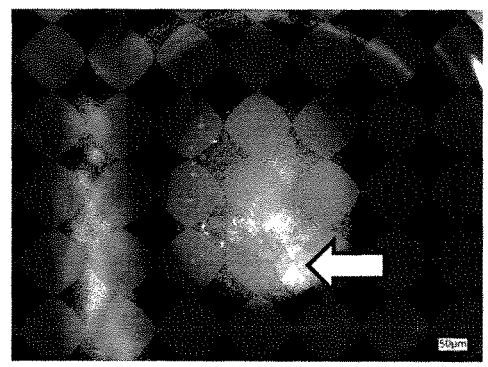
FIG. 18B is an image showing the intraocular conditions after the intravitreal administration of a SB328437 solution to an animal.
Figure 18C:
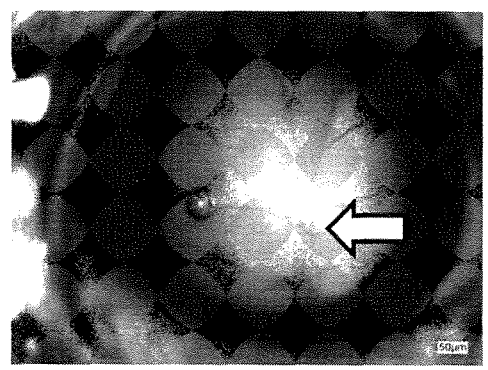
FIG. 18C is an image showing the intraocular conditions after the intravitreal administration of a GW766994 solution to an animal.
Figure 18D:
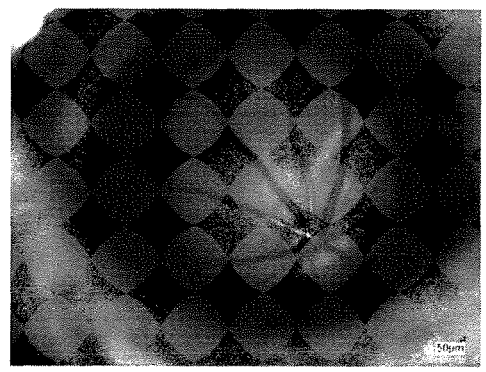
FIG. 18D is an image showing the intraocular conditions after the intravitreal administration of the composition of the present embodiment comprising Ki19003 and a CS derivative to an animal.
Figure 18E:
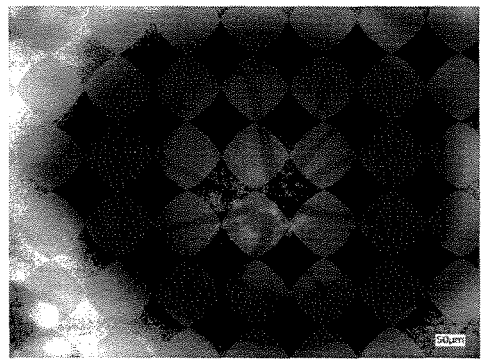
FIG. 18E is an image showing the intraocular conditions after the intravitreal administration of the composition of the present embodiment comprising GW766994 and a CS derivative to an animal.
Figure 18F:
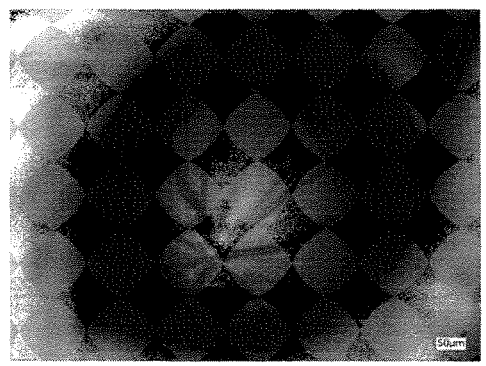
FIG. 18F is an image showing the intraocular conditions after the intravitreal administration of the composition of the present embodiment comprising Ki19003 and a CS derivative to an animal.
Figure 18G:
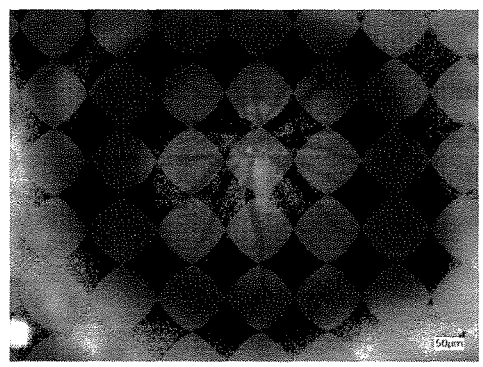
FIG. 18G is an image showing the intraocular conditions after the intravitreal administration of the composition of the present embodiment comprising Ki19003 and a CS derivative to an animal.
Figure 18H:
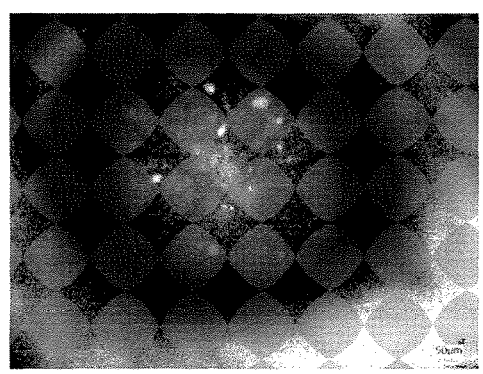
FIG. 18H is an image showing the intraocular conditions after the intravitreal administration of the composition of the present embodiment comprising SB328437 and an HA derivative to an animal.
Figure 19A:
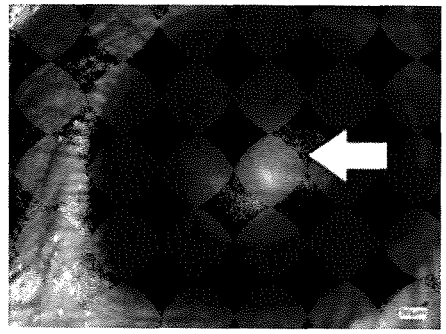
FIG. 19A is an image showing the intraocular conditions after the intravitreal administration of an RS504393 solution to an animal.
Figure 19B:
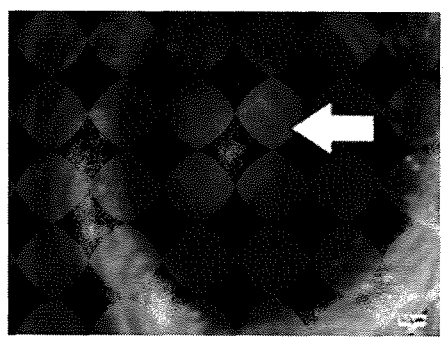
FIG. 19B is an image showing the intraocular conditions after the intravitreal administration of a PS372424 solution to an animal.
Figure 19C:
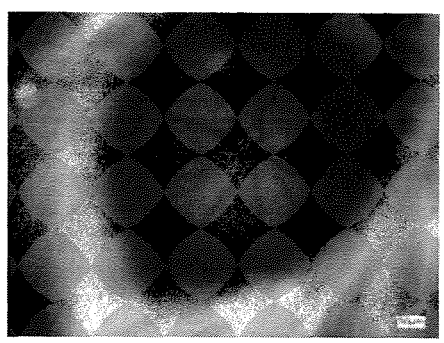
FIG. 19C is an image showing the intraocular conditions after the intravitreal administration of the composition of the present embodiment comprising RS504393 and an HA derivative to an animal.
Figure 19D:
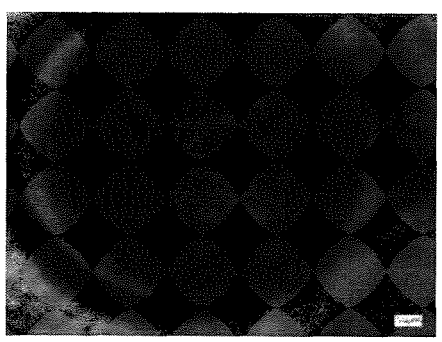
FIG. 19D is an image showing the intraocular conditions after the intravitreal administration of the composition of the present embodiment comprising PS372424 and an HA derivative to an animal.
Figure 19E:
FIG. 19E is an image showing the intraocular conditions after the intravitreal administration of the composition of the present embodiment comprising GW766994 and a CS derivative to an animal.
Figure 19F:
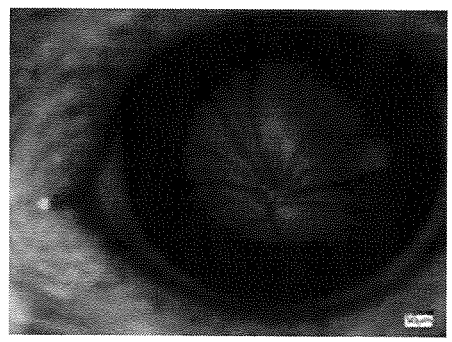
FIG. 19F is an image showing the intraocular conditions after the intravitreal administration of the composition of the present embodiment comprising GW766994 and a CS derivative to an animal.

The results of measurement of the CNV area are given in the table below and FIG. 17.

Compound 3 did not show significant inhibitory effects of CNV, as compared to CS.

TABLE 18

|  | mean | S.E. | n | Test results |
|---|---|---|---|---|
| CS | 50236 | 2371 | 8 |  |
| Compound 3 | 51925 | 2776 | 8 | N.S. |

N.S.: Not Significant (vs. CS), t-test

⟨Conclusions⟩

Like the administration of CS alone, administration of the cholanic acid-introduced CS alone did not show significant medicinal effects as a drug for treating age-related macular degeneration.

The entire disclosure of Japanese Patent Application No. 2015-110784 (filed: May 29, 2015) is incorporated herein by reference.

All publications, patent applications and technical standards mentioned in the present specification are incorporated herein by reference to the same extent as if each individual publication, patent application or technical standard was specifically and individually indicated to be incorporated by reference.

The invention claimed is:

1. A method for treating an age-related macular degeneration, comprising:
    administering a composition comprising a glycosaminoglycan derivative and a CCR3 antagonist or a pharmaceutically acceptable salt thereof into a vitreous body,
    wherein a concentration of the glycosaminoglycan derivative is 0.01 to 10 wt %,
    wherein the glycosaminoglycan derivative is a derivative of chondroitin sulfate in which a group derived from chondroitin sulfate is covalently bonded to a hydrophobic group,
    wherein an acidic functional groups of chondroitin sulfate may be in a free state not forming a salt or in a state forming a pharmaceutically acceptable salt, and
    wherein the CCR3 antagonist is a compound (II) represented by the following formula:

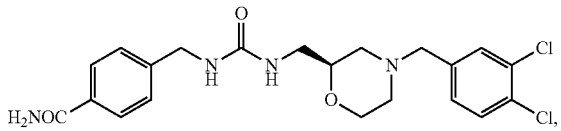

(II)

wherein the composition comprises the CCR3 antagonist as a sole compound effective for treating the age-related macular degeneration.

2. The method according to claim 1, wherein the derivative of chondroitin sulfate is a crosslinked chondroitin sulfate derivative.

3. The method according to claim 1, wherein the composition comprises a covalent complex of the derivative of chondroitin sulfate and the chemokine receptor activity regulator.

4. The method according to claim 1, wherein the hydrophobic group is at least one selected from the group consisting of a group derived from an alicyclic compound.

5. The method according to claim 4, wherein the hydrophobic group is at least one selected from the group consisting of a group derived from cholic acid, a group derived from lithocholic acid, a group derived from deoxycholic acid, and a group derived from cholanic acid.

6. The method according to claim 4, wherein the hydrophobic group is a group derived from 5β-cholanic acid.

7. The method according to claim 1, wherein a group derived from chondroitin sulfate is covalently bonded to the hydrophobic group via a spacer group.

8. The method according to claim 7, wherein the spacer group is —NH—$(CH_2)_m$—NH—, —C(=O)—$(CH_2)_m$—NH—, —C(=O)—$(CH_2)_m$—C(=O)—, —NH—$(CH_2)_m$—O—, —NH—$CH_2$—$(OCH_2)_m$—NH—, —NH—$CH_2$—$(OCH_2)_m$—O—, —C(=O)—$CH_2$—$(OCH_2)_m$—NH—, —C(=O)—$CH_2$—$(OCH_2)_m$—C(=O)—, —C(=O)—$(CH_2)_m$—O—, or —C(=O)—$CH_2$—$(OCH_2)_m$—O—,
    wherein each m independently represents an integer of 2 to 12.

9. The method according to claim 1, wherein the glycosaminoglycan derivative is a derivative of chondroitin sulfate in which a group derived from chondroitin sulfate is covalently bonded to a hydrophobic group with the proviso that the hydrophobic group does not comprise a fatty acid.

* * * * *

UNITED STATES PATENT AND TRADEMARK OFFICE
CERTIFICATE OF CORRECTION

PATENT NO. : 11,253,540 B2
APPLICATION NO. : 15/578034
DATED : February 22, 2022
INVENTOR(S) : Tomochika Kisukeda et al.

It is certified that error appears in the above-identified patent and that said Letters Patent is hereby corrected as shown below:

On the Title Page

Item (54), "COMPOSITION INCLUDING GLYCOSAMINOGLYCAN DERIVATIVE AND CHEMOKINE RECEPTOR ACTIVITY REGULATOR" should read -- COMPOSITION COMPRISING GLYCOSAMINOGLYCAN DERIVATIVE AND CHEMOKINE RECEPTOR ACTIVITY REGULATOR --.

In the Specification

Column 1, Line 1, "COMPOSITION INCLUDING GLYCOSAMINOGLYCAN DERIVATIVE AND CHEMOKINE RECEPTOR ACTIVITY REGULATOR" should read -- COMPOSITION COMPRISING GLYCOSAMINOGLYCAN DERIVATIVE AND CHEMOKINE RECEPTOR ACTIVITY REGULATOR --.

Column 6, Lines 12-13, "—NH—$(CH_2)_m$—NH—,—C(=O)—$(CH_2)_m$—NH—," should read -- —NH—$(CH_2)_m$—NH—, —C(=O)—$(CH_2)_m$—NH—, --.

Column 6, Lines 15-16, "—C(=O)—$(CH_2)_m$—C(=O)—,—NH—$(CH_2)_m$—O—," should read -- —C(=O)—$(CH_2)_m$—C(=O)—, —NH—$(CH_2)_m$—O—, --.

Column 6, Lines 18-19, "—NH—$CH_2$—$(OCH_2)_m$—NH—,—NH—$CH_2$—$(OCH_2)_m$—O—," should read -- —NH—$CH_2$—$(OCH_2)_m$—NH—, —NH—$CH_2$—$(OCH_2)_m$—O— --.

Column 6, Lines 25-26, "—C(=O)—$(CH_2)_m$—O,—C(=O)—$CH_2$—$(OCH_2)_m$—O—" should read -- —C(=O)—$(CH_2)_m$—O, —C(=O)—$CH_2$—$(OCH_2)_m$—O— --.

Column 8, Lines 42-43, "4-({[({[(2s)-4-(3,4-Dichlorobenyl)morpholin-2-yl]methyl}amino)carbonyl]amino}methyl)benzamide" should read -- 4-({[({[(2s)-4-(3,4-Dichlorobenzyl)morpholin-2-yl]methyl}amino)carbonyl]amino}methyl)benzamide --.

Signed and Sealed this
Seventh Day of June, 2022

Katherine Kelly Vidal
*Director of the United States Patent and Trademark Office*

CERTIFICATE OF CORRECTION (continued)
U.S. Pat. No. 11,253,540 B2

Column 8, Lines 52-53, "N-[[4-(3,4-Dichlorophenoxy)[1,4´-bipiperidine]-1´-yl]carbonyl]-4-methyl-benzensulfonamide" should read -- N-[[4-(3,4-Dichlorophenoxy)[1,4´-bipiperidine]-1´-yl]carbonyl]-4-methyl-benzenesulfonamide --.

Column 11, Line 29, "molecule" should read -- molecule. --.

Column 20, Line 49, "4.96) 1H, br-s)" should read -- 4.96 (1H, br-s) --.

Column 21, Line 40, "513328437" should read -- SB328437 --.

Column 32, Line 48, "(< Test Substances>" should read -- <Test Substances> --.

Column 34, Line 47, "Introocular" should read -- Intraocular --.

In the Claims

Column 42, Lines 32-39, "8. The method according to claim 7,
wherein the spacer group is —NH—$(CH_2)_m$—NH—,—C(=O)—$(CH_2)_m$—NH—,
—C(=O)—$(CH_2)_m$—C(=O)—,—NH—$(CH_2)_m$—O—,—NH—$CH_2$—$(OCH_2)_m$—NH—,
—NH—$CH_2$—$(OCH_2)_m$—O—,—C(=O)—$CH_2$—$(OCH_2)_m$—NH—,—C(=O)—$CH_2$—$(OCH_2)_m$—(C=O)—, —C(=O)—$(CH_2)_m$—O—,or —C(=O)—$CH_2$—$(OCH_2)_m$—O—,
wherein each m independently represents an integer of 2 to 12." should read -- 8. The method according to claim 7, wherein the spacer group is —NH—$(CH_2)_m$—NH—,
—C(=O)—$(CH_2)_m$—NH—,—C(=O)—$(CH_2)_m$—C(=O)—,—NH—$(CH_2)_m$—O—,
—NH—$CH_2$—$(OCH_2)_m$—NH—,—NH—$CH_2$—$(OCH_2)_m$—O—,
—C(=O)—$CH_2$—$(OCH_2)_m$—NH—,—C(=O)—$CH_2$—$(OCH_2)_m$—(C=O)—,
—C(=O)—$(CH_2)_m$—O—,or —C(=O)—$CH_2$—$(OCH_2)_m$—O—,
wherein each m independently represents an integer of 2 to 12. --.